(12) United States Patent
Andres et al.

(10) Patent No.: US 10,301,383 B2
(45) Date of Patent: May 28, 2019

(54) ANTIBODY SPECIFICALLY BINDING TO INSULIN-LIKE GROWTH FACTOR-1

(71) Applicant: Roche Diagnostics Operations, Inc., Indianapolis, IN (US)

(72) Inventors: Herbert Andres, Penzberg (DE); Hartmut Duefel, Schlehdorf (DE); Michael Gerg, Munich (DE); Frank Kowalewsky, Munich (DE); Christian Scholz, Penzberg (DE); Michael Schraemi, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 184 days.

(21) Appl. No.: 15/003,988

(22) Filed: Jan. 22, 2016

(65) Prior Publication Data
US 2016/0137728 A1    May 19, 2016

Related U.S. Application Data

(60) Division of application No. 14/069,445, filed on Nov. 1, 2013, now Pat. No. 9,273,144, which is a continuation of application No. PCT/EP2012/058208, filed on May 4, 2012.

(30) Foreign Application Priority Data

May 5, 2011  (EP) .................................... 11164957
Feb. 16, 2012  (EP) .................................... 12155742

(51) Int. Cl.
| | |
|---|---|
| C07K 16/00 | (2006.01) |
| C07K 16/22 | (2006.01) |
| C12N 9/90 | (2006.01) |
| C07K 16/12 | (2006.01) |
| G01N 33/74 | (2006.01) |
| C07K 16/40 | (2006.01) |
| G01N 33/573 | (2006.01) |
| C07K 14/475 | (2006.01) |
| C07K 14/65 | (2006.01) |

(52) U.S. Cl.
CPC ............ *C07K 16/22* (2013.01); *C07K 14/475* (2013.01); *C07K 14/65* (2013.01); *C07K 16/1203* (2013.01); *C07K 16/40* (2013.01); *C12N 9/90* (2013.01); *G01N 33/573* (2013.01); *G01N 33/74* (2013.01); *C07K 2317/34* (2013.01); *C07K 2317/565* (2013.01); *C07K 2317/92* (2013.01); *C07K 2319/00* (2013.01); *C07K 2319/21* (2013.01); *C07K 2319/22* (2013.01); *C07K 2319/23* (2013.01); *C07K 2319/24* (2013.01); *C07K 2319/35* (2013.01); *C07K 2319/41* (2013.01); *C07K 2319/43* (2013.01); *C12Y 502/01008* (2013.01); *G01N 2333/99* (2013.01)

(58) Field of Classification Search
None
See application file for complete search history.

(56) References Cited

U.S. PATENT DOCUMENTS

| 5,202,238 A | 4/1993 | Fell, Jr. et al. |
|---|---|---|
| 5,204,244 A | 4/1993 | Fell et al. |

FOREIGN PATENT DOCUMENTS

| EP | 0292656 A1 | 11/1988 |
|---|---|---|
| WO | 2007/077008 A1 | 7/2007 |
| WO | 2007/118214 A3 | 10/2007 |

OTHER PUBLICATIONS

Wu, Nie, Huse, and Watkins. Humanization of a murine monoclonal antibody by simultaneous optimization of framework and CDR residues. Journal of Molecular Biology, 1999. vol. 294, pp. 151-162.*
Skolnick and Fetrow. From genes to protein structure and function: novel applications of computational approaches in the genomic era. Trends in Biotechnology, 2000. vol. 18, pp. 34-39.*
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*
Bendig (1995) Methods: a companion methods in encymology 8: 83-93.*
Paul, Fundamental Immunology, 3rd edition, 1993, pp. 292-295.*
MacCallum et al. (1996) J. Mol. Biol. 262: 732-745.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
International Search Report dated Jul. 30, 2012, in Application No. PCT/EP2012/058208, 5 pages.
Baserga, Renato, "Oncogenes and the Strategy of Growth Factors," Cell, Dec. 1994, pp. 927-930, vol. 76.
Bendig, Mary M., "Humanization of Rodent Monoclonal Antibodies by CDR Grafting," Methods: A Companion to Methods in Enzymology, 1995, pp. 83-93, vol. 8.
Boerner, Paula et al., "Production of Antigen-Specific Human Monoclonal Antibodies From In Vitro-Primed Human Splenocytes," The Journal of Immunology, Jul. 1991, pp. 86-95, vol. 147, No. 1.
Casset, Florence et al., "A peptide mimetic of an anti-CD4 monoclonal antibody by rational design," Biochemical and Biophysical Research Communications, 2003, pp. 198-205, vol. 307.

(Continued)

*Primary Examiner* — Michael D Pak
(74) *Attorney, Agent, or Firm* — Roche Diagnostics Operations, Inc.

(57) ABSTRACT

Isolated antibodies that specifically bind to an epitope comprised in the stretch of amino acids ranging from amino acid 76 to amino acid 84 of human insulin-like growth factor-1 precursor (SEQ ID NO:1). Use of the novel antibodies for the sensitive and specific detection of insulin-like growth factor-1, in some embodiments while in the presence of high excess concentration of insulin-like growth factor-2, for example in a bodily fluid sample.

1 Claim, 17 Drawing Sheets

Specification includes a Sequence Listing.

(56) References Cited

OTHER PUBLICATIONS

Hoogenboom, Hennie R. and Winter, Greg, "By-passing Immunisation, Human Antibodies from Synthetic Repertoires of Germline VH Gene Segments Rearranged in Vitro," Journal of Molecular Biology, 1992, pp. 381-388, vol. 227.
Huston, James S. et al., "[3] Protein Engineering of Single-Chain Fv Analogs and Fusion Proteins," Methods in Enzymology, 1991, pp. 46-88, vol. 203.
Jakobovits, Aya et al., "Germ-line transmission and expression of a human-derived yeast artificial chromosome," Nature, Mar. 1993, pp. 255-258, vol. 362.
Jakobovits, Aya et al., "Analysis of homozygous mutant chimeric mice: Deletiopn of the immunoglobulin heavy-chain joining region blocks B-cell development and antibody production," Proceedings of the National Academy of Sciences USA, Mar. 1993, pp. 2551-2555, vol. 90.
Jones, John I. and Clemmons, David R., "Insulin-Like Growth Factors and Their Binding Proteins: Biological Actions," Endocrine Reviews, 1995, pp. 3-34, vol. 16, No. 1.
Koehler, G. and Milstein, C., "Continuous cultures of fused cells secreting antibody of predefined specificity," Nature, Aug. 1975, pp. 495-497, vol. 256.
MacCallum, Robert M. et al., "Antibody-antigen Interactions: Contact Analysis and Binding Site Topography," Journal of Molecular Biology, 1996, pp. 732-745, vol. 262.
Mañes, S. et al., "Physical mapping of human insulin-like growth factor-1 using specific monoclonal antibodies," Journal of Endocrinology, 1997, pp. 293-302, vol. 154.
Marks, James D. et al., "By-Passing Immunization: Human Antibodies from V-gene Libraries Displayed on Phage," Journal of Molecular Biology, 1991, pp. 581-597, vol. 222.
Morrison, Sherie L. et al., "Chimeric human antibody molecules: Mouse antigen-binding domains with human constant region domains," Proceedings of the National Academy of Sciences USA, Nov. 1984, pp. 6851-6855, vol. 81.
Neuberger, M. S. et al., "A hapten-specific chimaeric IgE antibody with human physiological effector function," Nature, Mar. 1985, pp. 268-270, vol. 314.
Pace, C. Nick et al., "How to measure and predict the molar absorption coefficient of a protein," Protein Science, 1995, pp. 2411-2423, vol. 4.
Paul, William E., Fundamental Immunology, Third Edition, 1993, pp. 292-295.
Riechmann, Lutz et al., "Reshaping human antibodies for therapy," Nature, Mar. 1988, pp. 323-327, vol. 332.
Rinderknecht, Ernst and Humbel, René E., "Polypeptides with nonsuppressible insulin-like and cell-growth promoting activities in human serum: Isolation, chemical characterization, and some biological properties of forms I and II," Proceedings of the National Academy of Sciences USA, Jul. 1976, pp. 2365-2369, vol. 73, No. 7.
Rinderknecht, Ernst and Humbel, René E., "The Amino Acid Sequence of Human Insulin-like Growth Factor I and Its Structural Homology with Proinsulin," The Journal of Biological Chemistry, 1978, pp. 2769-2776, vol. 253, No. 8.
Sara, Vicki R. and Hall, Kerstin, "Insulin-Like Growth Factors and Their Binding Proteins," Physiological Reviews, Jul. 1990, pp. 591-614, vol. 70, No. 3.
Schägger, Hermann and Von Jagow, Gebhard, "Tricine-Sodium Dodecyl Sulfate-Polyacylamide Gel Electrophoresis for the Separation of Proteins in the Range from 1 to 100 kDa," Analytical Biochemistry, 1987, pp. 368-379, vol. 166.
Sell, Christian et al., "Simian virus 40 large tumor antigen is unable to transform mouse embryonic fibroblasts lacking type 1 insulin-like growth factor receptor," Proceedings of the National Academy of Sciences USA, Dec. 1993, pp. 11217-11221, vol. 90.
Skolnick, Jeffrey and Fetrow, Jacquelyn S., "From genes to protein structure and function: novel applications of computational approaches in the genomic era," Trends in Biotechnology, 2000, pp. 34-39, vol. 18.
Ullrich, Axel et al., "Insulin-like growth factor I receptor primary structure: comparison with insulin receptor suggests structural determinants that define functional specificity," The EMBO Journal, 1986, pp. 2503-2512, vol. 5, No. 10.
Vajdos, Felix F. et al., "Comprehensive Functional Maps of the Antigen-binding Site of an Anti-ErbB2 Antibody Obtained with Shotgun Scanning Mutagenesis," Journal of Molecular Biology, 2002, pp. 415-428, vol. 320.
Van Dijk, Marc A. and Van De Winkel, Jan G. J., "Human antibodies as next generation therapeutics," Current Opinion in Chemical Biology, 2001, pp. 368-374, vol. 5.
Werner, Haim et al., "The Regulation of IGF-I Receptor Gene Expression," International Journal of Biochemistry & Cell Biology, 1995, pp. 987-994, vol. 27, No. 10.
Wu, Herren et al., "Humanization of a Murine Monoclonal Antibody by Simultaneous Optimization of Framework and CDR Residues," Journal of Molecular Biology, 1999, pp. 151-162, vol. 294.
Brüggemann, Marianne et al., Designer Mice: The Production of Human Antibody Repertoires in Transgenic Animals, Year in Immunology, 1993, pp. 33-40, vol. 7.
Cole, S .P. C. et al., The EBV-Hybridoma Technique and Its Application to Human Lung Cancer, Monoclonal Antibodies and Cancer Therapy, 1985, pp. 77-96.
Hintz, R. L. et al., Interaction of Somatomedin-C with an Antibody Directed Against the Synthetic C-Peptide Region of Insulin-Like Growth Factor-1, Journal of Clinical Endocrinology and Metabolism, 1980, pp. 405-407, vol. 50, No.
Lefranc, Marie-Paule, Nomenclature of the Human Immunoglobulin Genes, Current Protocols in Immunology, 2000, pp. A.1P.1-A.1P.37, Supplement 40.
Rinderknecht, Ernst and Humbel, Rene E., Primary Structure of Human Insulin-Like Growth Factor II, FEBS Letters, 1978, pp. 283-286, vol. 89, No. 2.
Tijssen, P., Preparation of enzyme-antibody or other enzyme-macromolecule conjugates, Practice and Theory of Enzyme Immunoassays, 1990, pp. 221-278, Ch. 11, Elsevier, Amsterdam.
Yamamoto, Kazumori et al., Analysis of Human IGF-1 by Elisa System.—Production and Characterization of Monoclonal Antibodies to IGF-1—, Clinical Chemistry and Enzymology Communications, 1996, pp. 155-165, vol. 7.

\* cited by examiner

FIG. 3

| mice no. | mice IC50 serum titer IC50 [mE] | |
|---|---|---|
| | IGF-1 | *T.thermophilus* SlyD-IGF-1(74-90) |
| K1643M1 | 800 | 10000 |
| K1643M2 | 1000 | 15000 |
| K1643M3 | 4700 | 50000 |
| K1643M4 | 500 | 7000 |
| K1643M5 | 2500 | 26000 |
| K1644M1 | 2800 | 32000 |
| K1644M2 | 280 | - |
| K1644M3 | 250 | 300 |
| K1644M4 | 150 | 800 |
| K1644M5 | 150 | - |

FIG. 4

| primary culture no. | reactivity [mE] | | |
|---|---|---|---|
| | IGF-1 | T.thermophilus SlyD-IGF-1(74-90) | T.thermophilus SlyD |
| 10.0.1 | 1013 | 957 | 347 |
| 10.0.2 | 217 | 127 | 45 |
| 10.0.3 | 941 | 1061 | 50 |
| 10.0.4 | 993 | 1023 | 900 |
| 10.0.5 | 998 | 1084 | 1023 |
| 10.0.6 | 32 | 56 | 55 |
| 10.0.7 | 988 | 1032 | 64 |
| 10.0.8 | 973 | 992 | 46 |
| 10.0.9 | 818 | 943 | 35 |
| 10.0.10 | 819 | 734 | 35 |
| 10.0.11 | 809 | 848 | 160 |
| 10.0.12 | 729 | 848 | 42 |
| 10.0.13 | 140 | 961 | 741 |
| 11.0.14 | 30 | 32 | 33 |
| 11.0.15 | 1087 | 1156 | 30 |
| 11.0.16 | 982 | 977 | 33 |
| 11.0.17 | 922 | 1021 | 28 | exemplary sensorgrams for <IGF-1>M-11.0.15

FIG. 6

| clone culture | reactivity [mE] | | |
|---|---|---|---|
| | IGF-1 | T.thermophilus SlyD-IGF-1(74-90) | T.thermophilus SlyD |
| 10.1.3 | 2748 | 2116 | 37 |
| 10.2.3 | 2768 | 2112 | 40 |
| 10.3.7 | 2712 | 2091 | 32 |
| 10.4.7 | 2700 | 2109 | 35 |
| 10.5.8 | 2501 | 1993 | 35 |
| 10.6.8 | 2410 | 1955 | 36 |
| 10.7.9 | 2111 | 1899 | 36 |
| 10.8.9 | 2145 | 1911 | 38 |
| 11.9.15 | 2578 | 2389 | 32 |
| 11.10.15 | 2585 | 2396 | 33 |
| 11.11.17 | 2427 | 2154 | 32 |
| 11.12.17 | 2372 | 2142 | 32 |

Captured mAb<IGF1>M-11.11.17-IgG vs. IGF-1 (native)

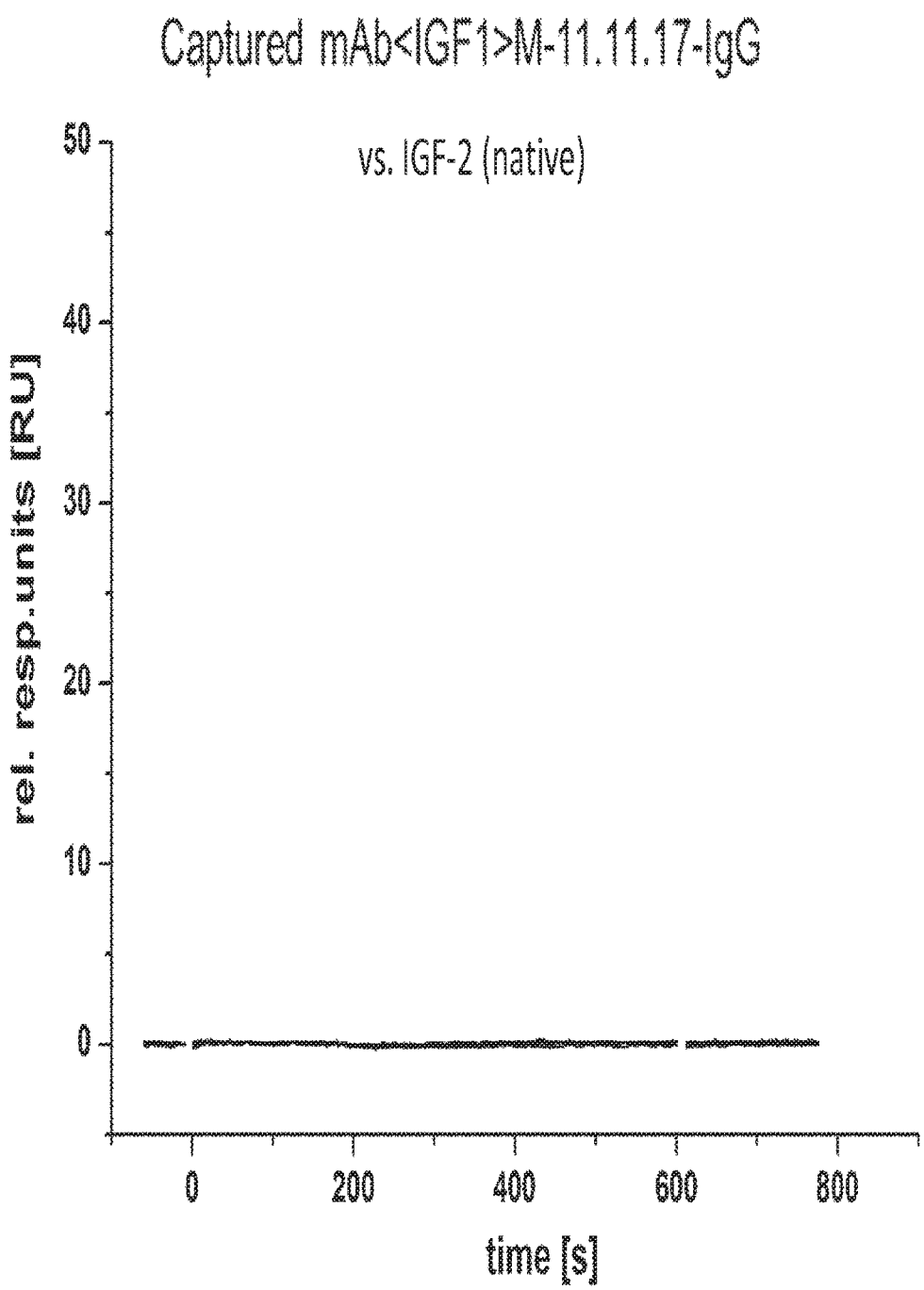

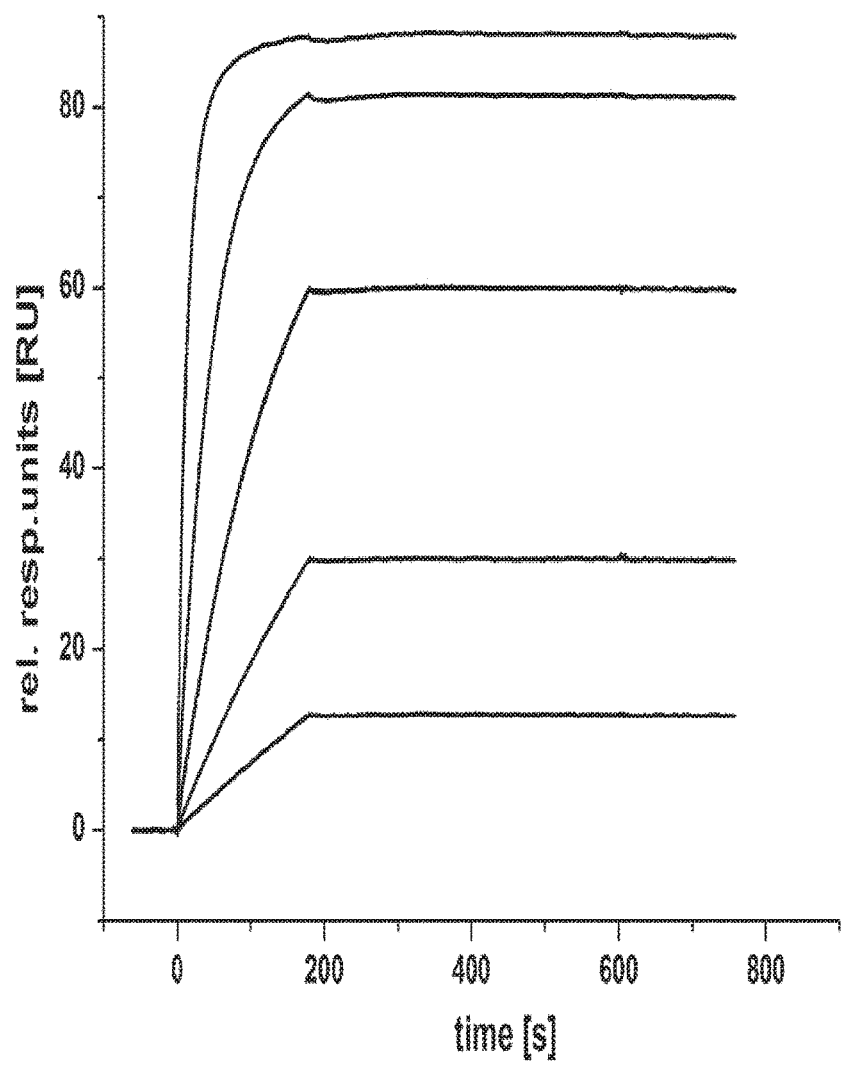

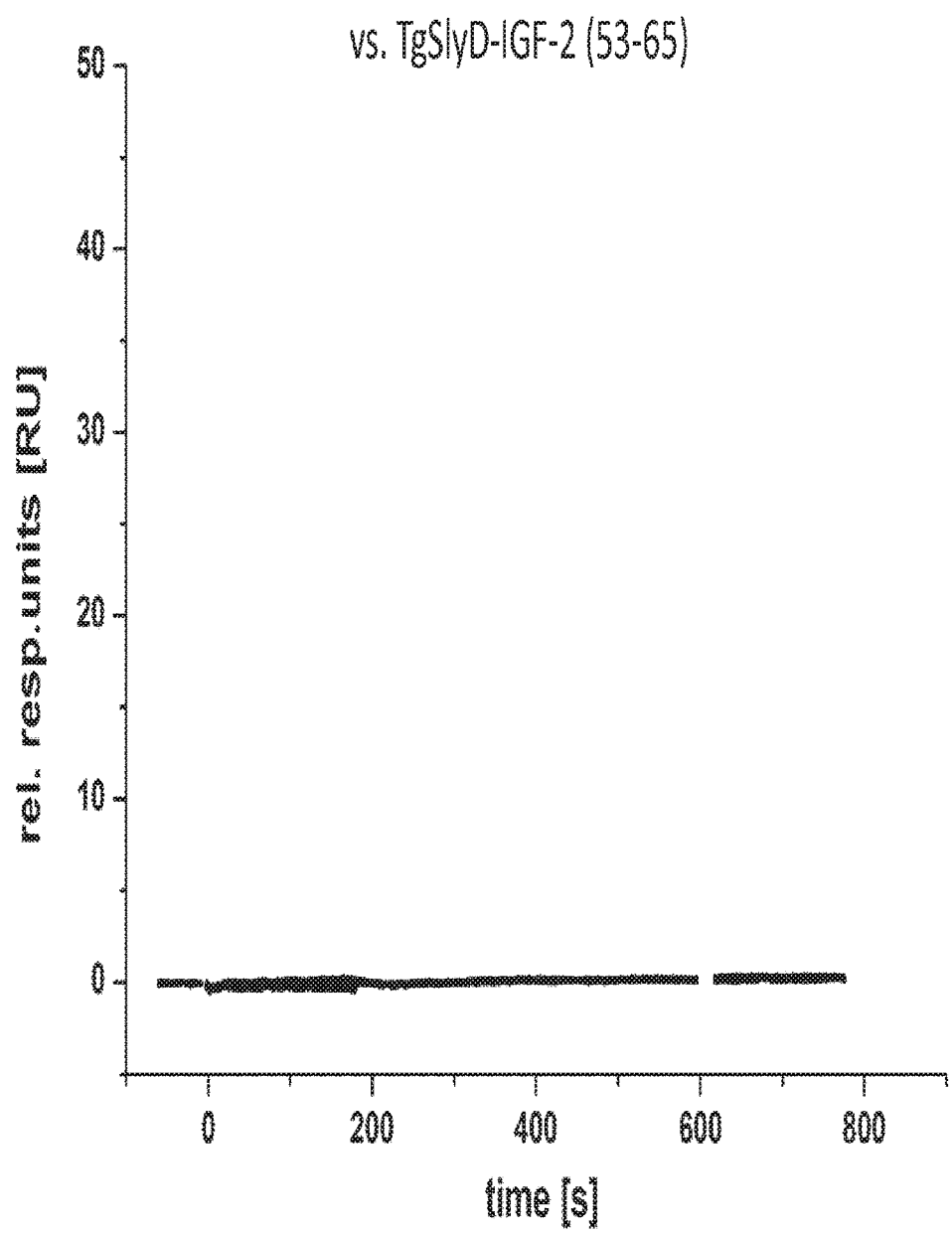

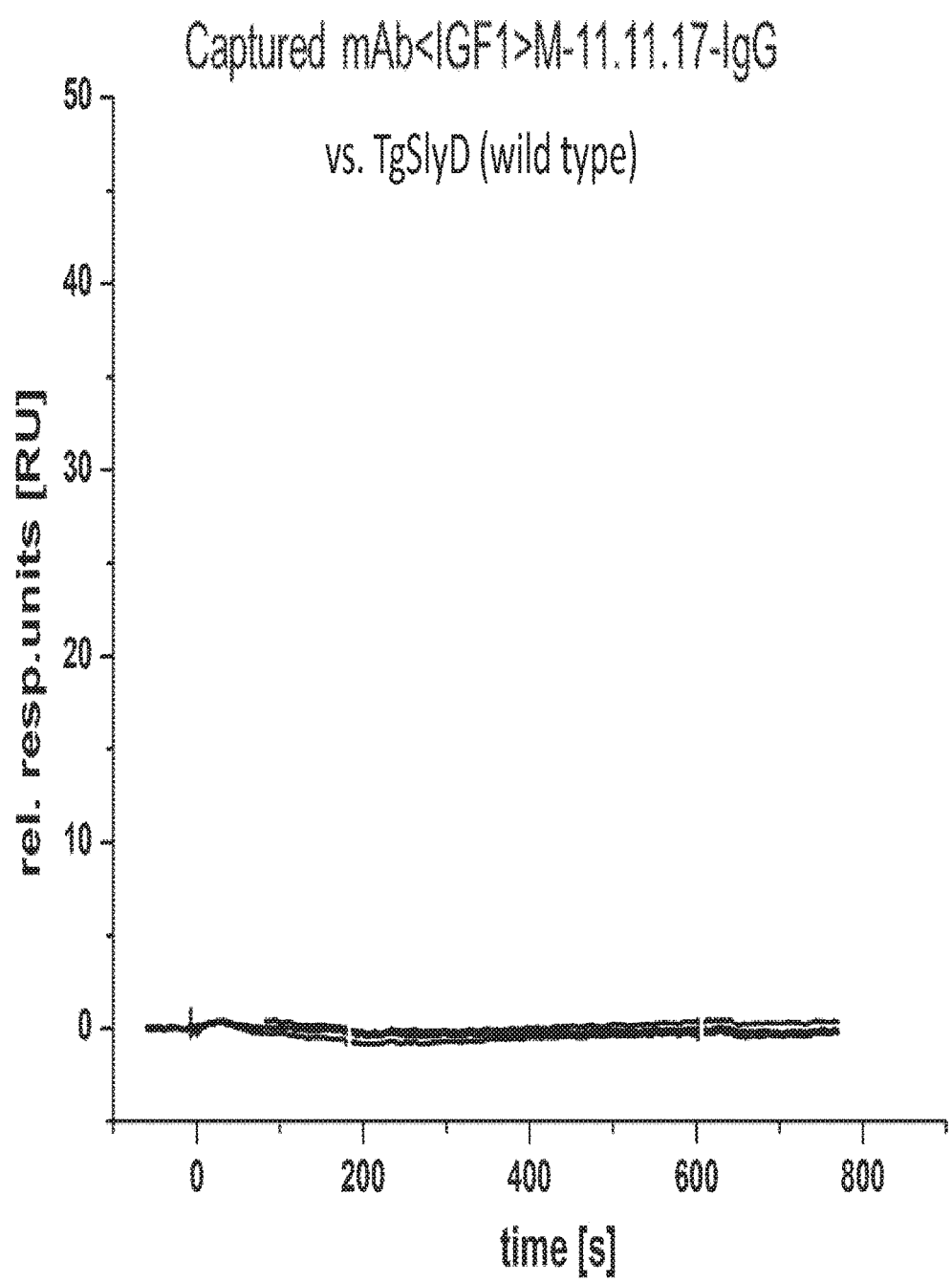

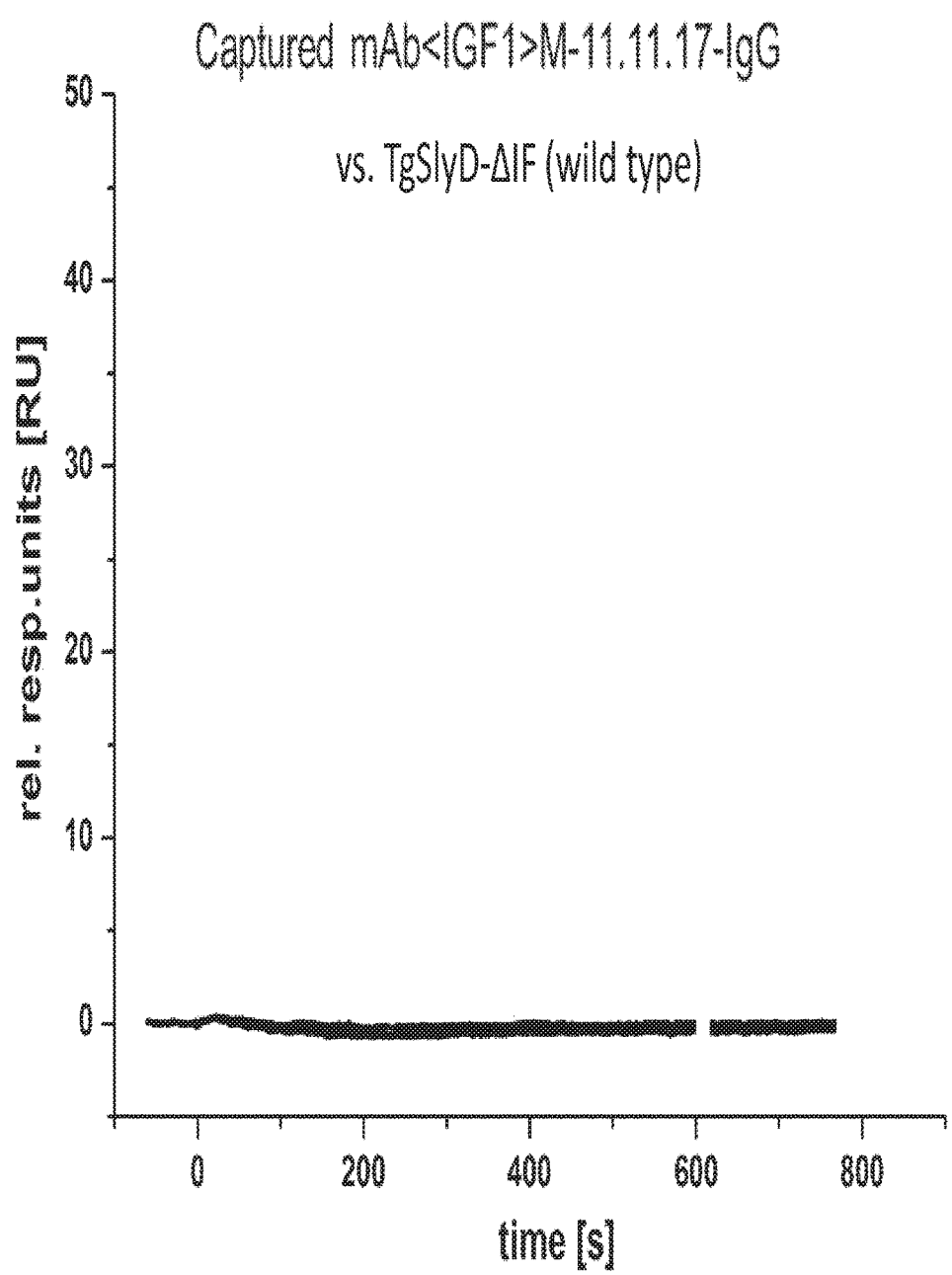

FIG. 8

| mAb | RU | Antigen | kDa | °C | $k_a$ 1/Ms | $k_d$ 1/s | $t_{1/2}$-diss min | $K_D$ nM | $R_{max}$ RU | MR | Chi² RU² |
|---|---|---|---|---|---|---|---|---|---|---|---|
| M-11.11.17 | 457 | IGF-I (native) | 8 |  | 2,0E+06 | 2,1E-05 | 560 | 0,01 | 46 | 2,0 | 0,0 |
|  | 439 | IGF-II (native) | 8 |  | n.d. | n.d. | n.d. | n.d. | n.d. | n.d. | n.d. |
|  | 432 | TtSlyD-IGF-1(74-90) | 14 |  | 7,1E+05 | 1,0E-05 | 1113 | 0,01 | 83 | 2,0 | 0,0 |
|  | 427 | TgSlyD-IGF-2(53-65) | 14 | 25 | n.d. | n.d. | n.d. | n.d. | n.d. | n.d. | n.d. |
|  | 421 | TtSlyD-wt | 18 |  | n.d. | n.d. | n.d. | n.d. | n.d. | n.d. | n.d. |
|  | 419 | TgSlyD-wt | 18 |  | n.d. | n.d. | n.d. | n.d. | n.d. | n.d. | n.d. |
|  | 418 | TgSlyD-dIF-wt | 15 |  | n.d. | n.d. | n.d. | n.d. | n.d. | n.d. | n.d. |
| M-10.7.9 | 512 | hIGF-I (native) | 8 |  | 9,2E+05 | 1,5E-03 | 8 | 1,6 | 44 | 1,7 | 0,0 |
|  | 494 | hIGF-II (native) | 8 |  | n.d. | n.d. | n.d. | n.d. | n.d. | n.d. | n.d. |
|  | 485 | TtSlyD-IGF-1(74-90) | 14 |  | 2,9E+05 | 6,9E-04 | 17 | 2,4 | 84 | 1,8 | 0,0 |
|  | 479 | TgSlyD-IGF-2(53-65) | 14 | 25 | n.d. | n.d. | n.d. | n.d. | n.d. | n.d. | n.d. |
|  | 470 | TtSlyD-wt | 18 |  | n.d. | n.d. | n.d. | n.d. | n.d. | n.d. | n.d. |
|  | 468 | TgSlyD-wt | 18 |  | n.d. | n.d. | n.d. | n.d. | n.d. | n.d. | n.d. |
|  | 465 | TgSlyD-dIF-wt | 15 |  | n.d. | n.d. | n.d. | n.d. | n.d. | n.d. | n.d. |
| M-2.28.44 | 731 | hIGF-I (native) | 8 |  | 3,9E+06 | 1,3E-04 | 92 | 0,03 | 68 | 1,8 | 0,0 |
|  | 717 | hIGF-II (native) | 8 |  | 4,9E+06 | 2,4E-03 | 5 | 0,5 | 67 | 1,8 | 0,3 |
|  | 704 | TtSlyD-IGF-1(74-90) | 14 |  | n.d. | n.d. | n.d. | n.d. | n.d. | n.d. | n.d. |
|  | 693 | TgSlyD-IGF-2(53-65) | 14 | 25 | n.d. | n.d. | n.d. | n.d. | n.d. | n.d. | n.d. |
|  | 673 | TtSlyD-wt | 18 |  | n.d. | n.d. | n.d. | n.d. | n.d. | n.d. | n.d. |
|  | 664 | TgSlyD-wt | 18 |  | n.d. | n.d. | n.d. | n.d. | n.d. | n.d. | n.d. |
|  | 655 | TgSlyD-dIF-wt | 15 |  | n.d. | n.d. | n.d. | n.d. | n.d. | n.d. | n.d. |

ANTIBODY SPECIFICALLY BINDING TO INSULIN-LIKE GROWTH FACTOR-1

CROSS-REFERENCE TO RELATED APPLICATIONS

This application is a divisional of U.S. application Ser. No. 14/069,445 filed Nov. 1, 2013, which is a continuation of International Application No. PCT/EP2012/058208 filed May 4, 2012, which claims the benefit of European Patent Application No. 11164957.0 filed May 5, 2011 and European Patent Application No. 12155742.5 filed Feb. 16, 2012, the disclosures of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Oct. 23, 2013, is named SEQUENCE_LISTING_30927US.txt, and is twenty-eight thousand eight hundred and fifty-one bytes in size.

BACKGROUND

Human Insulin-like Growth Factor-1, (UniProtKB entry P05019, IGF1_human, (SEQ ID NO:1)) also known as somatomedin C and somatomedin A, is in its mature form a 70 amino acid polypeptide (SEQ ID NO:2), that shares large stretches of sequence identity and high structural homology with IGF-2 and insulin (Rinderknecht, E. and Humbel, R. E., Proc. Natl. Acad. Sci. USA 73 (1976) 2365-2369; Rinderknecht, E. and Humbel, R. E., J. Biological Chemistry 253 (1978) 2769-2776). Human IGF-2 is present in human serum with a 500-fold molar excess over IGF-1 (Jones, J. I. and Clemmons, D. R., Endocr. Rev. 16 (1995) 3-34). The higher serum concentration of IGF-2 and its sequence homology with IGF-1 are major obstacles to the specific immunological detection of IGF-1.

Similar to insulin, the IGF-1 polypeptide chain can be divided into domains. IGF-1 comprises four domains, B (amino acid residues 1-29), C (30-41), A (42-62) and D (63-70), respectively. Domains A and B are structural homologs of insulin B and A chains, respectively, domain C is analogous to the connecting peptide of proinsulin, while the D-domain has no counterpart in insulin.

As summarized by Manes S., et al., J. Endocrinol. 154 (1997) 293-302, IGF-1 is thought to mediate the growth-promoting activity of growth hormone (GH) (Sara, V. R. and Hall, K., Physiol Rev. 70 (1990) 591-614). It is also considered critical in local control of cell growth, differentiation and survival in a variety of cell types through a paracrine or autocrine pathway (Jones J. I. and Clemmons, D. R., Endocrin. Rev. 16 (1995) 3-34). The putative receptor for IGF-1, the type-1 IGF receptor (IGF-1R) (Ullrich, A., et al., EMBO J., 5 (1986) 2503-2512), has been proposed to play a key role in tumorigenesis (Sell, C., et al., Proc. Natl. Acad. Sci. USA 90 (1993) 11217-11221). There is ample evidence indicating that many tumors express IGF-1R and produce and secrete IGF-1 or IGF-2 to the extracellular milieu (Baserga, R., Cell 79 (1994) 927-930; Werner, H., et al., Int. J. Biochem. Cell Biol. 27 (1995) 987-994), thereby promoting continuous cell growth in an autocrine fashion.

Both IGF-1 and IGF-2 are expressed in numerous tissues and cell types and may have autocrine, paracrine and endocrine functions. Mature IGF-1 and IGF-2 are highly conserved between the human, bovine and porcine proteins (100% identity), and also exhibit cross-species activity. The IGFL (insulin-like growth factor-like) family includes four small (~11 kDa) family members in humans and one in mouse.

SUMMARY OF THE DISCLOSURE

It has surprisingly been found that antibodies binding to a rather short partial sequence of insulin-like growth factor-1 (IGF-1), i.e. to amino acids 76 to 84 (SEQ ID NO:3) of the IGF-1 precursor, represented by SEQ ID NO:1, have quite advantageous properties and can overcome at least some of the problems known in the art.

In one embodiment the present disclosure relates to an isolated antibody binding to an epitope comprised within amino acids 76-84 (SEQ ID NO:3) of insulin-like growth factor-1 precursor.

In one embodiment of the present disclosure, monoclonal antibodies binding to an epitope comprised in SEQ ID NO:3, or to a partial sequence within this stretch (SEQ ID NO:4) of amino acids, e.g. ranging from amino acids 77 to 84 of the IGF-1 precursor (SEQ ID NO:1) are disclosed.

As disclosed and described herein, the methods and antibodies provided and disclosed herein are of significant value in research, therapeutic and diagnostic applications.

The present disclosure also relates to partial sequences of antibodies specifically binding to IGF-1 and to an immunoassay method, the method comprising the steps of incubating a liquid sample with an antibody according to the present disclosure, whereby binding of said antibody to insulin-like growth factor-1 in said sample takes place and detecting the IGF-1 bound to the anti-insulin-like growth factor-1 antibody in said sample.

BRIEF DESCRIPTION OF THE DRAWINGS

The features of this disclosure, and the manner of attaining them, will become more apparent and the disclosure itself will be better understood by reference to the following description of embodiments of the disclosure taken in conjunction with the accompanying drawing.

FIG. 3 presents serum titers in mice after 12 weeks of immunization determined by ELISA using *Thermus thermophilus* SlyD-IGF-1(74-90) and human IGF-1 (=IGF-1), as capture antigens, respectively (mE=milli Absorbance).

FIG. 4 presents an ELISA screen of primary cultures showing binding signals versus IGF-1, *Thermus thermophilus* SlyD-IGF-1(74-90) fusion polypeptide and *Thermus thermophilus* wild type SlyD polypeptide (mE=milli Absorbance, IGF-1=human IGF-1).

FIG. 6 presents an ELISA screen of clone culture supernatants versus IGF-1, *Thermus thermophilus* SlyD-IGF-1 (74-90) fusion polypeptide and *Thermus thermophilus* wild type SlyD polypeptide. Increased absorption signals indicative of improved binding affinity were detected with IGF-1 and the *Thermus thermophilus* SlyD-IGF-1(74-90) fusion polypeptide.

FIG. 7B presents BIAcore measurements of <IGF-1>M-11.11.17-IgG versus IGF-2 polypeptide.

FIG. 7C presents BIAcore measurements of <IGF-1>M-11.11.17-IgG versus *Thermus thermophilus* SlyD-IGF-1(74-90) fusion polypeptide.

FIG. 7D presents BIAcore measurements of <IGF-1>M-11.11.17-IgG versus *Thermococcus gammatolerans* SlyD-IGF-2 (53-65) fusion polypeptide.

FIG. 7F presents BIAcore measurements of <IGF-1>M-11.11.17-IgG versus *Thermococcus gammatolerans* wild-type SlyD polypeptide.

FIG. 7G presents BIAcore measurements of <IGF-1>M-11.11.17-IgG versus *Thermus thermophilus* SlyD-ΔIF fusion polypeptide.

FIG. 8 is a table with binding kinetics of newly developed anti IGF-1 antibodies (mAb: monoclonal antibody; RU: Relative response unit of monoclonal antibody captured on the sensor; Antigen: antigen in solution; kDa: molecular weight of the antigens injected as analytes in solution; $k_a$: association rate constant; $k_d$: dissociation rate constant; $t_{1/2\ diss}$: antibody-antigen complex half-life calculated according to the formula $t_{1/2\ diss}=\ln(2)/60*k_d$; $K_D$: dissociation constant; $R_{MAX}$: Binding signal at the end of the association phase of the 90 nM analyte injection; MR: Molar Ratio; Chi$^2$: chi-squared-test of the measurement; n.d.: not detectable).

Figure 1:
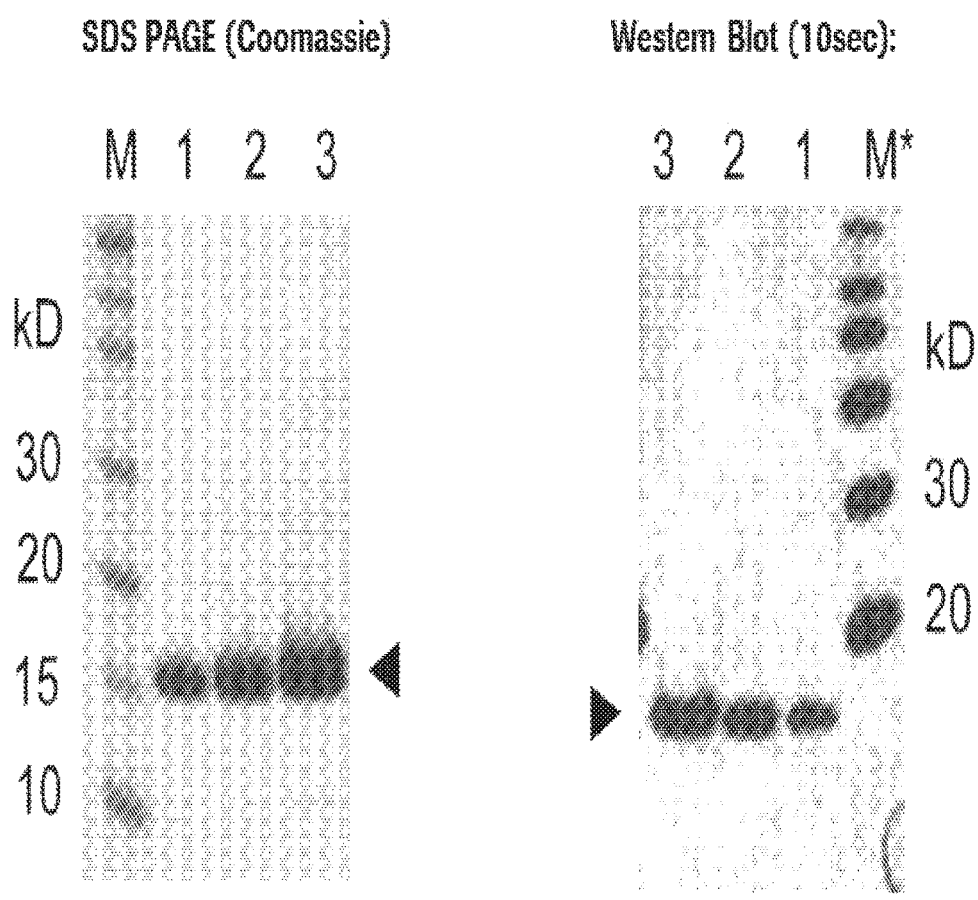
FIG. 1 presents a SDS PAGE (Coomassie staining) and anti-his-tag Western Blot (10 sec exposition) of *Thermus thermophilus* SlyD-IGF-1(74-90) fusion polypeptide. M—Novex Sharp Standard; 1-2.5 µg *Thermus thermophilus* SlyD-IGF-1(74-90) fusion polypeptide; 2-5.0 µg *Thermus thermophilus* SlyD-IGF-1(74-90) fusion polypeptide; 3-10 µg *Thermus thermophilus* SlyD-IGF-1(74-90) fusion polypeptide; M*—Magic Mark.

Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

BRIEF DESCRIPTION OF THE SEQUENCE LISTING

SEQ ID NO. 1: provides the sequence of human insulin-like growth factor-1 precursor.
SEQ ID NO. 2: provides the sequence of mature human insulin-like growth factor-1.
SEQ ID NO. 3: provides a partial sequence of human insulin-like growth factor-1 precursor (positions 76 to 84).
SEQ ID NO. 4: provides a partial sequence of human insulin-like growth factor-1 precursor (positions 77 to 84).
SEQ ID NO. 5: provides a partial sequence of human insulin-like growth factor-1 precursor (positions 74 to 90).
SEQ ID NO. 6: provides an artificial sequence: (gly-gly-gly-ser).
SEQ ID NO. 7: provides an artificial sequence: (His-tag).
SEQ ID NO. 8: provides an artificial sequence: FkBP-IGF-1(74-90) fusion protein.
SEQ ID NO. 9: provides an artificial sequence: SlyD-FkBP-IGF-1(74-90) fusion protein.
SEQ ID NO. 10: provides an artificial sequence: *Thermus thermophilus*-SlyD-IGF-1(74-90) fusion protein.
SEQ ID NO. 11: provides an artificial sequence: *Thermus thermophile* wild-type SlyD protein.
SEQ ID NO. 12: provides an artificial sequence: *Thermus thermophilus* SlyD lacking the IF domain.
SEQ ID NO. 13: provides an artificial sequence: *Thermococcus gammatolerans* SlyD-IGF-1 (74-90) fusion protein.
SEQ ID NO. 14: provides an artificial sequence: *Thermococcus gammatolerans* SlyD-IGF-2 (53-65) fusion protein.
SEQ ID NO. 15: is heavy chain CDR3H of MAb 10.07.09.
SEQ ID NO. 16: is heavy chain CDR2H of MAb 10.07.09.
SEQ ID NO. 17: is heavy chain CDR1H of MAb 10.07.09.
SEQ ID NO. 18: is light chain CDR3H of MAb 10.07.09.
SEQ ID NO. 19: is light chain CDR2H of MAb 10.07.09.
SEQ ID NO. 20: is light chain CDR1H of MAb 10.07.09.
SEQ ID NO. 21: is heavy chain variable domain VH of MAb 10.07.09.
SEQ ID NO. 22: is light chain variable domain VL of MAb 10.07.09.
SEQ ID NO. 23: is heavy chain CDR3H of MAb 11.11.17.
SEQ ID NO. 24: is heavy chain CDR2H of MAb 11.11.17.
SEQ ID NO. 25: is heavy chain CDR1H of MAb 11.11.17.
SEQ ID NO. 26: is light chain CDR3H of MAb 11.11.17.
SEQ ID NO. 27: is light chain CDR2H of MAb 11.11.17.
SEQ ID NO. 28: is light chain CDR1H of MAb 11.11.17.
SEQ ID NO. 29: is heavy chain variable domain VH of MAb 11.11.17.
SEQ ID NO. 30: is light chain variable domain VL of MAb 11.11.17.
SEQ ID NO. 31: is heavy chain variable domain VH of MAb 11.09.15.
SEQ ID NO. 32: is light chain variable domain VL of MAb 11.09.15.
SEQ ID NOs. 33-64: provide partial sequences of human insulin-like growth factor-1 precursor as used in epitope analysis.

Although the sequence listing represents an embodiment of the present disclosure, the sequence listing is not to be construed as limiting the scope of the disclosure in any manner and may be modified in any manner as consistent with the instant disclosure and as set forth herein.

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

Mature human insulin-like growth factor-1 (IGF-1) has a molecular weight of about 8 kDa and consists of 70 amino acids. IGF-1 comprises four well defined regions, B (amino acid residues 1-29), C (30-41), A (42-62) and D (63-70) of SEQ ID NO. 2, respectively.

In serum detection of IGF-1, most instruments use stringent washing steps to reduce and overcome unspecific binding of the specific binding agents, e.g. antibodies, used therein. Commonly, antibodies developed by immunization with native IGF-1 recognize their genuine immunogen with higher affinity and antigen complex stability than they recognize IGF-2, which cross-reacts with lower affinity and antigen complex stability. For example, the murine monoclonal antibody <IGF-1>-M 2.28.44, which has been derived from an immunization campaign of mice with native recombinant human IGF-1 shows a binding kinetic signature (see FIG. 8) versus IGF-1 with $K_D=0.03\times10^{-9}$ mol/L affinity and $t_{1/2\ diss}=92$ min whereas IGF-2 is bound with $K_D=5\times10^{-9}$ mol/L affinity and $t_{1/2\ diss}=5$ min. The fundamental difference lies in the antigen complex stabilities. The successful use of such an antibody for an IGF-1 specific assay, is strongly dependent on the instrument's washing setup, since it is required to deplete IGF-2 from the <IGF-1>-M 2.28.44 cross-reactive antibody. In brief, the technical limitations of IGF-1 binding antibodies exhibiting cross-reactivity to IGF-2 can only be overridden by means of sophisticated washing steps.

It is self-evident, that IGF-1 specificity requirements are much higher for an antibody applied under equilibrium conditions, in particular in a diagnostic system, which does not perform any washing or purification procedures of the antibody-antigen immune complexes. Among other embodiments, also the in vivo situation is principally characterized by a thermodynamic equilibrium.

The present disclosure discloses an antibody that overcomes the problems known in the art and meets the key demand for an IGF-1 specific antibody, suitable for application under equilibrium conditions, and not only recognizes IGF-1 (with high affinity) but also does not detect IGF-2 association $k_a$ (1/Ms) even at high IGF-2 serum concentrations.

In principle, immunological discrimination between IGF-1 and IGF-2 should only be feasible when the respective antibody targets an IGF-1 epitope which clearly differs in amino acid sequence or conformation from the IGF-2 counterpart. Indeed, there is only one conspicuous sequential deviation between IGF-1 and IGF-2, notably in the turn-loop motif of IGF-1 at the IGF-1 amino acid position 74-90, starting the numbering with the signal and propeptide (UniProtKB entry P05019, IGF1_human). Hitherto, it has not been possible to obtain antibodies targeting this IGF-1 motif as an epitope by conventional immunization strategies using native IGF-1 as an immunogen in experimental animals.

The present disclosure relates to a novel isolated antibody that specifically binds to this genuine IGF-1 epitope within the stretch of amino acids ranging from amino acid 76 to amino acid 84 of the human insulin-like growth factor-1 precursor (SEQ ID NO:1). The novel antibodies disclosed herein are of great utility since they allow for the sensitive and highly specific detection of insulin-like growth factor-1 even in the presence of large excess of the closely related IGF-2.

Surprisingly, it has been found and is disclosed herein that it is possible to exploit and engineer the amino acid stretch from amino acid 76 to amino acid 90 (SEQ ID NO:5) of human insulin-like growth factor-1 precursor (SEQ ID NO:1) into a surrogate immunogen, thereby paving the way for the generation of antibodies specifically binding to the C-domain of native IGF-1. We also find, that an isolated antibody binding to an epitope comprised within amino acids 76 to amino acid 84 of human insulin-like growth factor-1 precursor (SEQ ID NO:1) can be used with great advantage in the immunological detection of IGF-1.

Based on the surprising disclosure provided herein, some embodiments of the present disclosure relate to an isolated antibody binding to an epitope comprised within the loop region of insulin-like growth factor-1 (SEQ ID NO:5). In some embodiments, the present disclosure relates to an isolated antibody binding within amino acid residues 76-84 (SEQ ID NO:3) of insulin-like growth factor-1 precursor (SEQ ID NO:1). In other words, an isolated antibody according to the present disclosure binds to an epitope comprised in SEQ ID NO:3.

Unless otherwise explained, all technical and scientific terms used herein have the same meaning as commonly understood by one of ordinary skill in the art to which the disclosure disclosed herein belongs.

The articles "a" and "an" are used herein to refer to one or to more than one (i.e., to at least one) of the grammatical object of the article. By way of example, "an antibody" means one antibody or more than one antibody.

An "epitope" is a site on a target molecule (e.g., an antigen, such as a protein or nucleic acid molecule) to which an antigen-binding molecule (e.g., an antibody, antibody fragment, scaffold protein containing antibody binding regions, or aptamer) binds. Epitopes can be formed both from contiguous or adjacent noncontiguous residues (e.g., amino acid residues) of the target molecule. Epitopes formed from contiguous residues (e.g., amino acid residues) typically are also called linear epitopes. An epitope typically includes at least 5 and up to about 12 residues, mostly between 6 and 10 residues (e.g. amino acid residues). An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified to greater than 70% by weight of antibody as determined by, for example, the Lowry method, and in some embodiments, to greater than 80%, 90%, 95%, 96%, 97%, 98% or 99% by weight. In some exemplary embodiments the isolated antibody according to the present disclosure is purified to greater than 90% purity as determined by SDS-PAGE under reducing conditions using Coomassie blue staining for protein detection.

In some embodiments the antibody according to the present disclosure is a polyclonal antibody. A polyclonal antibody binding to a sequence comprised in SEQ ID NO:3 can, for example, be obtained by immunoadsorption using an affinity column containing this sequence as immunosorbent material. In some embodiments, the antibody according to the present disclosure is a monoclonal antibody.

Prior to the instant disclosure, it has not been possible to generate antibodies to the C-domain of IGF-1 at all. Indeed, immunization with native recombinant IGF-1 as well as immunization with IGF-1 derived peptides (Manes S., et al., J. Endocrinol. 154 (1997) 293-302) failed to produce monoclonal antibodies versus the epitope region identified by the antibodies of the instant disclosure. Most notably, immunization of experimental animals with the linear polypeptide sequence comprising the amino acids 76 to 84 of insulin-like growth factor-1 precursor, failed to generate antibodies, neither exhibiting binding activity for the native conformational IGF-1, nor for its linear peptide motif. Additionally, earlier attempts to synthesize sufficient amounts of a constrained IGF-1 peptide comprising the amino acid sequences 76 to 84 of insulin-like growth factor-1 precursor, for the purpose of immunization of experimental animals, were unsuccessful. Based on the novel methods disclosed herein previously non-accessible antibodies can now be generated in a reproducible fashion.

In brief, the method shown herein comprises the use of an engineered *Thermus thermophilus* SlyD. The SlyD IF (Insert-In-Flap) substrate binding domain is replaced by the amino acid sequence 76 to 84 from the insulin-like growth factor-1 precursor, thus constituting a thermostable scaffold module with a grafted peptide immunogen. The amino acid graft is presented by the *Thermus thermophilus* SlyD FKBP domain in a constrained, enthalpically favored way, which retains the native-like secondary structure of the IGF-1 insertion motif. This chimeric polypeptide is used as an immunogen for the immunization of experimental animals. The humoral immune response towards the complete polypeptide is also targeted to the insertion motif. By comparative screening (e.g. versus the wild type chaperone or versus native mature IGF-1) antibodies can now be selected which specifically recognize the IGF-1 insertion motif. The chimeric polypeptide, as disclosed herein, serves as a surrogate polypeptide for native IGF-1 and surprisingly enables for the first time direct-ability of the immune response towards a preselected epitope in order to generate high affinity antibodies.

As used herein, the terms "binding to human IGF-1", or "anti-IGF-1 antibody" are interchangeable. The antibody binding to the human IGF-1 antigen according to the present disclosure will, in at least some embodiments, have a $K_D$-value of $1.0\times10^{-8}$ mol/l or lower at 25° C., and in one embodiment a $K_D$-value of $1.0\times10^{-9}$ mol/l or lower at 25° C. The binding affinity is determined with a standard binding assay, such as surface plasmon resonance technique (BIAcore®, GE-Healthcare Uppsala, Sweden). A method for determining the $K_D$-value of the binding affinity is described in the Examples Section. Thus an "antibody binding to human IGF-1" as used herein refers to an antibody binding to the human IGF-1 antigen with a $K_D$ of at least $K_D$ $1.0\times10^{-8}$ mol/l or lower, and in some cases a of $K_D$ $1.0\times10^{-9}$ mol/l to $K_D$ $10\times10^{-12}$ mol/l at 25° C. The binding affinity $K_D$ is determined using a T200 instrument (GE Healthcare, Biacore).

The antibodies described herein do not show any measurable association rate constant $k_a$ (1/Ms) at 25° C. versus IGF-2. The antibodies show an association rate constant $k_a$ (1/Ms) versus IGF-1 from at least $k_a$ $9\times10^5$ (1/Ms) or faster, nearby the diffusion limit. Thus in one embodiment the antibodies according to the present disclosure do not show a measurable association rate constant at 25° C. to IGF-2. In some embodiments the antibodies according to the present disclosure also show antigen complex stabilities from at least $k_d$ $2\times10^{-3}$ (1/s) to $k_d$ $3\times10^{-5}$ (1/s) at 25° C. or slower.

As the skilled artisan will appreciate the term "specific" is used to indicate that other biomolecules present in the sample do not significantly bind to the antibody that is specifically binding to the biomolecule of interest (for example, insulin-like growth factor-1). In some embodiments, the level of binding to a biomolecule other than insulin-like growth factor-1 results in a negligible (e.g., not determinable) binding affinity by means of ELISA or an affinity determination, for example when using a Biacore 4000 instrument.

As noted above, the antibody of the instant disclosure which specifically binds to insulin-like growth factor-1 does not bind to insulin-like growth factor-2. More precisely, kinetic measurements using a highly sensitive Biacore T200 instrument do not show any determinable association rate constant $k_a$ (1 Ms) of such antibody versus IGF-2, even at high analyte concentrations (see e.g. FIGS. 7A-G). Furthermore, the antibody "specifically binding to insulin-like growth factor-1" is characterized by a fully functional stoichiometric binding of IGF-1 at 25° C., in a way that one antibody is able to bind simultaneously to two IGF-1 polypeptides, indicated by Molar Ratio (MR) values from MR=1.7 to MR=2.0 (cf. FIG. 8).

Binding Affinity $K_D$ Determination of an Antibody.

An exemplary embodiment by which the binding affinity $K_D$ of an antibody using a T200 instrument (GE Healthcare, Biacore) may be determined according to the instant disclosure is provided. A Biacore T200 instrument (GE Healthcare) is used to kinetically assess the hybridoma culture supernatants for binding specificity to IGF-1 peptides. A CM5 series S sensor is mounted into the system and was normalized in HBSN buffer (10 mM HEPES pH 7.4, 150 mM NaCl) according to the manufacturer's instructions. The system buffer is changed to HBS-ET (10 mM HEPES pH 7.4, 150 mM NaCl, 0.05% TWEEN 20). The sample buffer is the system buffer supplemented with 1 mg/ml CMD (Carboxymethyldextran, Sigma #86524). The system operates at 25° C.

10000 RU RAMIgGFC (relative units of rabbit-anti-mouse F(c)gamma-fragment of the respective mouse immunoglobulin G subclass/Jackson Laboratories) are immobilized according to the manufacturer's instructions using EDC/NHS chemistry on the flow cells FC1 (anti-mouse F(c)gamma of subclass 1), FC2, FC3 and FC4 The sensor is deactivated using 1M ethanolamine.

The binding activity of the antibody against the peptide of e.g. SEQ ID NO:3 (IGF-1 76-84) is kinetically tested. Antibodies are captured by a 1 min injection at 10 μl/min of crude hybridoma supernatants diluted 1:3 in sample buffer.

The flow rate is set to 100 μl/min. The peptide e.g. of SEQ ID NO: (IGF-1-precursor positions 76-84) is injected at different concentration steps of 0 nM, 1.1 nM, 3. nM, 10 nM, 30 nM and 90 nM, respectively, for 3 min. The dissociation is monitored for 600 sec using a Kinject command. Acidic regeneration of the sensor surface is achieved using 3 consecutive injections of 10 mM Glycine pH 1.5 at 30 μl/min for 30 sec.

In some embodiments the antibody according to the present disclosure specifically binds to an epitope comprised within the amino acid sequence of SEQ ID NO:3, i.e. to an epitope comprised within amino acids 76 to 84 of insulin-like growth factor-1 precursor (SEQ ID NO:1) with a $K_D$-value of $1.0\times10^{-8}$ mol/l or lower at 25° C. As mentioned above, polyclonal antibodies according to the present disclosure, i.e. binding to an epitope comprised in SEQ ID NO:3 can e.g. be isolated from the serum of an immunized animal by immunoadsorption using the peptide of SEQ ID NO:3 for immunosorption.

Monoclonal antibodies can be produced with constant quality and in almost unlimited quantity. In some exemplary embodiments the antibody binding to an epitope comprised in SEQ ID NO:3 is a monoclonal antibody.

In some embodiments the antibody binding to SEQ ID NO:3 is the monoclonal antibody produced by the hybridoma cell line 10.07.09 (producing the MAb<h-IGF-1>M-10.07.09).

Two of the <IGF-1> monoclonal antibodies newly generated (11.11.17 producing the MAb<h-IGF-1>M-11.11.17 and 11.09.15 producing the MAb<h-IGF-1>M-11.09.15, respectively) bind to an even smaller epitope comprised within SEQ ID NO:3, i.e. they bind to the epitope represented by SEQ ID NO:4.

In some embodiments the antibody of the present disclosure binds to an epitope comprising the amino acids 76 to 84 of insulin-like growth factor-1 precursor, i.e. to amino acids 28 to 36 of the mature IGF-1, (SEQ ID NO:4). In some embodiments the antibody of the present disclosure binds to the synthetic 15-mer peptides of SEQ ID NO: 43 through SEQ ID NO: 49, i.e. to those peptides comprising an epitope consisting of the amino acids 76 to 84 of insulin-like growth factor-1 precursor (SEQ ID NO:3).

In some embodiments the antibody of the present disclosure binds to an epitope comprising the amino acids 77 to 84 of insulin-like growth factor-1 precursor (SEQ ID NO:4). In some embodiments the antibody of the present disclosure binds to the synthetic 15-mer peptides of SEQ ID NO:43 through SEQ ID NO:50, i.e. to those peptides comprising an epitope consisting of the amino acids 77 to 84 of insulin-like growth factor-1 (SEQ ID NO:4).

Whether an antibody binds to an epitope of the amino acid sequence given in SEQ SEQ ID NO:3 or SEQ ID NO:4, respectively, may be assessed by PepScan-analysis as described in the Examples section. Binding to the epitope of SEQ ID NO:3 is, for example, acknowledged if the various PepScan peptides comprising the sequence of SEQ ID NO:3 test positive with the antibody under investigation in such analysis.

The disclosure also relates an antibody specifically binding to IGF-1, characterized in comprising as heavy chain variable domain CDR3 region a CDR3 region of SEQ ID NO:15.

For example, the antibody specifically binding to IGF-1 may be characterized in that the heavy chain variable domain comprises a CDR3 region of SEQ ID NO:15 and a CDR2 region of SEQ ID NO:16.

In some embodiment, the antibody specifically binding to IGF-1 may be characterized in that the heavy chain variable domain comprises a CDR3 region of SEQ ID NO:15, a CDR2 region of SEQ ID NO:16 and a CDR1 region of SEQ ID NO:17.

The disclosure also relates to an antibody which binds to human IGF-1 characterized in that the heavy chain variable domain comprises a CDR3H region of SEQ ID NO:15, a CDR2H region of SEQ ID NO:16, and a CDR1H region of SEQ ID NO:17, and the light chain variable domain comprises a CDR3L region of SEQ ID NO:18, a CDR2L region of SEQ ID NO:19, and a CDR1 L region of SEQ ID NO:20.

Also, according to some embodiments, the disclosure provides an antibody characterized in that the heavy chain variable domain VH is SEQ ID NO:21; and the light chain variable domain VL is SEQ ID NO:22, respectively, or a humanized version thereof. The disclosure also relates an antibody specifically binding to IGF-1, characterized in comprising a heavy chain variable domain CDR3 region of SEQ ID NO:23.

According to some embodiments, the antibody specifically binding to IGF-1 may be characterized in that the heavy chain variable domain comprises a CDR3 region of SEQ ID NO:23 and a CDR2 region of SEQ ID NO:24. In some embodiments, the antibody specifically binding to IGF-1 may be characterized in that the heavy chain variable domain comprises a CDR3 region of SEQ ID NO:23, a CDR2 region of SEQ ID NO:24 and a CDR1 region of SEQ ID NO:25.

In some embodiment, the disclosure also relates to an antibody which binds to human IGF-1 characterized in that the heavy chain variable domain comprises a CDR3H region of SEQ ID NO:23, a CDR2H region of SEQ ID NO:24, and a CDR1H region of SEQ ID NO:25, and the light chain variable domain comprises a CDR3L region of SEQ ID NO:26, a CDR2L region of SEQ ID NO:27, and a CDR1 L region of SEQ ID NO:28.

The disclosure further relates an antibody characterized in that the heavy chain variable domain VH is SEQ ID NO:29; and the light chain variable domain VL is SEQ ID NO:30, respectively, or a humanized version thereof. In some embodiments the disclosure also relates to an antibody characterized in that the heavy chain variable domain VH is SEQ ID NO:31; and the light chain variable domain VL is SEQ ID NO:32, respectively, or a humanized version thereof.

In some embodiments, the antibody according to the disclosure is monoclonal. In some embodiments the antibody according to the disclosure is humanized or human. In some embodiment the antibody according to the disclosure is of the IgG1 or the IgG4 subclass. In some embodiments the antibody according to the disclosure is a monoclonal humanized antibody of the IgG1 subclass. Further, the disclosure also relates to chimaeric or the humanized antibodies comprising the HCDR3 of SEQ ID NO:15, or SEQ ID NO:23, respectively, for example.

The term "antibody" encompasses the various forms of antibody structures including, but not being limited to, whole antibodies and antibody fragments. The antibody according to the disclosure may be a human antibody, a humanized antibody, a chimeric antibody, or further genetically engineered antibody as long as the characteristic properties according to the disclosure are retained.

"Antibody fragments" comprise a portion of a full length antibody, for example possibly a variable domain thereof, or at least an antigen binding site thereof. Examples of antibody fragments include diabodies, single-chain antibody molecules, and multispecific antibodies formed from antibody fragments. scFv antibodies are, e.g., described in Huston, J. S., Methods in Enzymol. 203 (1991) 46-88. In addition, antibody fragments comprise single chain polypeptides having the characteristics of a $V_H$ domain, namely being able to assemble together with a $V_L$ domain, or of a $V_L$ domain binding to IGF-1, namely being able to assemble together with a $V_H$ domain to a functional antigen binding site and thereby providing the properties of an antibody according to the disclosure.

The terms "monoclonal antibody" or "monoclonal antibody composition" as used herein refer to a preparation of antibody molecules of a single amino acid composition.

The term "chimeric antibody" refers to a monoclonal antibody comprising a variable region, i.e., binding region, from mouse and at least a portion of a constant region derived from a different source or species, usually prepared by recombinant DNA techniques. Chimeric antibodies comprising a mouse variable region and a human constant region are exemplary embodiments. Such mouse/human chimeric antibodies are the product of expressed immunoglobulin genes comprising DNA segments encoding mouse immunoglobulin variable regions and DNA segments encoding human immunoglobulin constant regions. Other forms of "chimeric antibodies" encompassed by the present disclosure are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., Proc. Natl. Acad Sci. USA 81 (1984) 6851-6855; U.S. Pat. Nos. 5,202,238 and 5,204,244.

The term "humanized antibody" or "humanized version of an antibody" refers to antibodies in which the framework or "complementarity determining regions" (CDR) have been modified to comprise the CDR of an immunoglobulin of different specificity as compared to that of the parent immunoglobulin. In some exemplary embodiments, the CDRs of the VH and VL are grafted into the framework region of human antibody to prepare the "humanized antibody." See e.g. Riechmann, L., et al., Nature 332 (1988) 323-327; and Neuberger, M. S., et al., Nature 314 (1985) 268-270. The heavy and light chain variable framework regions can be derived from the same or different human antibody sequences. The human antibody sequences can be the sequences of naturally occurring human antibodies. Human heavy and light chain variable framework regions are listed e.g. in Lefranc, M.-P., Current Protocols in Immunology (2000)—Appendix 1P A.1P.1-A.1P.37 and are accessible via IMGT, the international ImMunoGeneTics information System® (http://imgt.cines.fr) or via http://vbase.mrc-cpe.cam.ac.uk, for example. Optionally the framework region can be modified by further mutations. Exemplary CDRs correspond to those representing sequences recognizing the antigens noted above for chimeric antibodies. In some embodiments, such humanized version is chimerized with a human constant region. The term "humanized antibody" as used herein also comprises such antibodies which are modified in the constant region to generate the properties according to the disclosure, especially in regard to C1q binding and/or FcR binding, e.g. by "class switching" i.e. change or mutation of Fc parts (e.g. from IgG1 to IgG4 and/or IgG1/IgG4 mutation).

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germline immunoglobulin gene array in such germ-line mutant mice results in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Brueggemann, M. D., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole, A., et al. and Boerner, P., et al. are also available for the preparation of human monoclonal antibodies (Cole, A., et al., Monoclonal Antibodies and Cancer Therapy, Liss, A. R. (1985) p. 77; and Boerner, P., et al., J. Immunol. 147 (1991) 86-95). As already mentioned, according to the instant disclosure the term "human antibody" as used herein also comprises such antibodies which are modified in the constant region to generate the properties according to the disclosure, for example in regard to C1q binding and/or FcR binding, e.g. by "class switching" i.e. change or mutation of Fc parts (e.g. from IgG1 to IgG4 and/or IgG1/IgG4 mutation).

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the disclosure have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The antibodies according to the present disclosure have proven extremely useful in the detection of insulin-like growth factor-1 from a liquid sample by aid of an immunoassay. Immunoassays are well known to the skilled artisan. Methods for carrying out such assays as well as practical applications and procedures are summarized in related textbooks. Examples of related textbooks are Tijssen, P., Preparation of enzyme-antibody or other enzyme-macromolecule conjugates, In: Practice and Theory of Enzyme Immunoassays, pp. 221-278, Burdon, R. H. and v. Knippenberg, P. H. (eds.), Elsevier, Amsterdam (1990), and various volumes of Methods in Enzymology, Colowick, S. P., and Caplan, N. O. (eds.), Academic Press), dealing with immunological detection methods, especially volumes 70, 73, 74, 84, 92 and 121.

In some embodiments, methods according to the present disclosure include measuring IGF-1 protein in an immunoassay procedure. In certain embodiments IGF-1 is detected in an enzyme-linked immunosorbent assay (ELISA) or in an electrochemiluminescence-based immunoassay (ECLIA). In some embodiments IGF-1 is detected in a sandwich assay (sandwich-type assay format). In some embodiments the measurement of IGF-1 is performed in a sandwich immunoassay employing at least two antibodies reactive with at least two non-overlapping epitopes.

In some embodiments the present disclosure relates to methods for detecting IGF-1 in a body fluid sample via a sandwich immunoassay, the method comprising the steps of incubating the sample with an antibody according to this disclosure, whereby binding of said antibody to insulin-like growth factor-1 comprised in said sample takes place, incubating the sample with a second antibody to IGF-1 binding to an epitope not comprising amino acids 76 to 84 of IGF-1, whereby binding of the second antibody takes place and measuring the immunological sandwich complex formed in steps (a) and (b), thereby detecting IGF-1 in the sample.

Sandwich assays are commonly used assays. A number of variations of the sandwich assay technique exist, and all are intended to be encompassed by the present disclosure. Briefly, in a typical forward assay, an unlabeled antibody is immobilized on a solid substrate (or solid phase), and the sample to be tested is brought into contact with the bound molecule. Immobilization of this capture antibody can be by direct adsorption to a solid phase or indirectly, e.g. via a specific binding pair, e.g. via the streptavidin-biotin binding pair. After a suitable period of incubation, for a period of time sufficient to allow formation of an antibody-antigen complex, a second antibody binding to the antigen, labeled with a reporter molecule capable of producing a detectable signal is then added and incubated, allowing time sufficient for the formation of a sandwich-complex of antibody-antigen-labeled antibody. Any unreacted material is washed away, and the presence of the IGF-1 is determined by observation of a signal produced by the reporter molecule. The results may either be qualitative, by simple observation of the visible signal, or may be quantitated by comparing with a control sample containing known amounts of biomarker.

In a typical sandwich assay a first antibody is either bound covalently or non-covalently to a solid surface. The solid surface is typically glass or a polymer, the most commonly used polymers being cellulose, polyacrylamide, nylon, polystyrene, polyvinyl chloride, or polypropylene. The solid supports may be in the form of tubes, beads, discs of microplates, or any other surface suitable for conducting an immunoassay. The binding processes are well-known in the art and generally consist of cross-linking, covalent binding, or physically adsorbing. The antibody-coated solid surface ("solid phase complex") is usually treated to block non-specific binding and washed in preparation for the test sample. An aliquot of the sample to be tested is then added to the solid phase complex and incubated for a period of time sufficient (e.g. 2-40 minutes or overnight if more convenient) and under suitable conditions (e.g., from room temperature to 40° C. such as between 25° C. and 32° C. inclusive) to allow for binding between the first or capture antibody and the corresponding antigen. Following the incubation period, the solid phase, comprising the first or capture antibody and bound thereto the antigen is washed, and incubated with a secondary or labeled antibody binding to another epitope on the antigen. The second antibody is linked to a reporter molecule which is used to indicate the binding of the second antibody to the complex of first antibody and the antigen of interest.

Variations on the assay include a simultaneous assay, in which both sample and labeled antibody are added simultaneously to the bound antibody or the antibody capable of being bound to a solid phase. These techniques are well known to those skilled in the art, including any minor variations as will be readily apparent.

An alternative, competitive method involves immobilizing IGF-1 on a solid phase and then exposing the immobilized target together with the sample to a specific antibody to IGF-1, which may or may not be labeled with a reporter molecule. Depending on the amount of target and the strength of the reporter molecule signal, a competition by the target molecule may be detectable directly via such labeled antibody. Alternatively, the antibody specifically binding to IGF-1 can be immobilized and IGF-1 can be determined via competition of IGF-1 in a sample with labelled IGF-1.

In some exemplary embodiments, the method(s) according to the present disclosure is (are) practiced using a bodily fluid as sample material. In further exemplary embodiments the bodily fluid sample is selected from whole blood, serum or plasma. In some embodiments, the immunoassays for measurement of IGF-1 uses urine as a sample material.

For use in detection of IGF-1, kits or articles of manufacture are also provided by the disclosure. These kits may comprise a carrier means being compartmentalized to receive in close confinement one or more container means such as vials, tubes, and the like, each of the container means comprising one of the separate elements to be used in the method. For example, one of the container means may comprise an antibody according to the present disclosure. The kit may also have containers comprising a reporter-means, such as a second antibody binding to IGF-1 bound to a reporter molecule, such as an enzymatic, florescent, or radioisotope label. Such kit will typically comprise the containers described above and one or more other containers comprising materials desirable from a commercial and user standpoint, including buffers, diluents, filters, needles, syringes, and package inserts with instructions for use. A label may be present on the container to indicate that the composition is used for a specific application, and may also indicate directions for use.

In one further specific embodiment, for antibody-based kits, the kit can comprise, for example: (1) a first antibody (e.g., attached to a solid support or capable of binding to a solid support) that specifically binds to IGF-1; and (2) a second, different antibody that binds to the IGF-1. In some embodiments the later antibody is labeled with a reporter molecule. In some embodiments the first for the second antibody are exchanged in a vice versa manner when designing such assay.

The following examples, sequence listing, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

Illustrative Embodiments

The following comprises a list of illustrative embodiments according to the instant disclosure which represent various embodiments of the instant disclosure. These illustrative embodiments are not intended to be exhaustive or limit the disclosure to the precise forms disclosed, but rather, these illustrative embodiments are provided to aide in further describing the instant disclosure so that others skilled in the art may utilize their teachings.

1. An isolated antibody binding to an epitope comprised within amino acids 76-84 (SEQ ID NO:3) of insulin-like growth factor-1 precursor (SEQ ID NO: 1).

2. The antibody of embodiment 1, wherein said antibody is a monoclonal antibody.

3. The antibody of embodiment 2, wherein said antibody is characterized in that the heavy chain variable domain comprises a CDR3 region of SEQ ID NO:15.

4. The antibody of embodiment 1 or 2, wherein said antibody is characterized in that the heavy chain variable domain comprises a CDR3 region of SEQ ID NO:15, a CDR2 region of SEQ ID NO:16 and a CDR1 region of SEQ ID NO:17.

5. The antibody of embodiment 2, wherein said antibody is characterized in that the heavy chain variable domain comprises a CDR3H region of SEQ ID NO:15, a CDR2H region of SEQ ID NO:16, and a CDR1H region of SEQ ID NO:17, and the light chain variable domain comprises a CDR3L region of SEQ ID NO:18, a CDR2L region of SEQ ID NO:19, and a CDR1 L region of SEQ ID NO:20.

6. The antibody of embodiment 1, wherein said antibody binds to an epitope comprised within the amino acids 77 to 84 (SEQ ID NO:4) of insulin-like growth factor-1 precursor (SEQ ID NO:1).

7. The antibody of embodiment 6, wherein said antibody is a monoclonal antibody.

8. The antibody of embodiment 7, wherein said antibody is characterized in that the heavy chain variable domain comprises a CDR3 region of SEQ ID NO:23.

9. The antibody of embodiment 7, wherein said antibody is characterized in that the heavy chain variable domain comprises a CDR3 region of SEQ ID NO:23, a CDR2 region of SEQ ID NO:24 and a CDR1 region of SEQ ID NO:25.

10. The antibody of embodiment 7, wherein said antibody is characterized in that the heavy chain variable domain comprises a CDR3H region of SEQ ID NO:23, a CDR2H region of SEQ ID NO:24, and a CDR1H region of SEQ ID NO:25, and the light chain variable domain comprises a CDR3L region of SEQ ID NO:26, a CDR2L region of SEQ ID NO:27, and a CDR1L region of SEQ ID NO:28.

11. A method for detecting IGF-1 in a body fluid sample via a sandwich immunoassay, the method comprising the steps of
  a) incubating the sample with an antibody according to any of embodiments 1 to 10, whereby binding of said antibody to insulin-like growth factor-1 comprised in said sample takes place,
  b) incubating the sample with a second antibody to IGF-1 binding to an epitope not comprising amino acids 76 to 84 of IGF-1 precursor, whereby binding of the second antibody takes place and
  c) measuring the immunological sandwich complex formed in steps (a) and (b), thereby detecting IGF-1 in the sample.

EXAMPLES

Example 1. General Procedure for Generation of Monoclonal Antibodies

The pre-formulated fusion polypeptide immunogen is administered to an experimental animal, such as mouse, rat, rabbit, sheep, or hamster, intraperitoneally at different dosages. Prior to collection of the B-cells a boost immunization is performed. B-cell hybridomas can be obtained according to the method of Koehler and Milstein (Koehler, G. and Milstein, C., Nature 256 (1975) 495-497). The hybridomas obtained are deposited as single clones or cells in the wells of a multi well plate. Primary hybridoma cultures that are tested positive with respect to the binding of the antibody by the secreted antibody are further screened with a kinetic screening method.

Example 2. Generation of Antibodies to Insulin-Like Growth Factor-1 Using a SlyD/FKBP12-IGF-1(74-90) Fusion Polypeptide In the generation of monoclonal antibodies to IGF-1, fusion polypeptides comprising the amino acid sequence (SEQ ID NO: 5)
NKPTGYGSSSRRAPQTG can be used for the immunization of laboratory animals.

In order to improve the presentation of the immunogenic polypeptide, the IGF-1 turn-loop motif of SEQ ID NO: 5 can be flanked either by a GGGS linker (SEQ ID NO:6) N-terminal and C-terminal of the amino acid sequence or by an HG dipeptide N-terminal of the IGF-1 amino acid sequence and by a GA dipeptide C-terminal of the IGF-1 amino acid sequence.

A SlyD/FKBP12-IGF-1(74-90) fusion polypeptide was used as immunogen and also as screening reagent for the development of an anti-IGF-1 antibody that is specifically binding to the IGF-1 amino acid sequence consisting of (SEQ ID NO: 5)
NKPTGYGSSSRRAPQTG.

An FKBP12-IGF-1(74-90) fusion polypeptide also comprising an amino acid sequence tag of SEQ ID NO:7 has the following amino acid sequence:

(SEQ ID NO: 8)
MGVQVETISPGDGRTFPKRGQTAVVHYTGMLEDGKKFDSSRDRNKPFKF

MLGKQEVIRGWEEGVAQMSVGQRAKLTISPDYAYGGGGSNKPTGYGSSS

RRAPQTGGGSTLVFDVELLKLEGGGSRKHHHHHHHH.

The SlyD/FKBP12-IGF-1(74-90) fusion polypeptide comprising an amino acid sequence tag of SEQ ID NO:7 has the following amino acid sequence:

(SEQ ID NO: 9)
MKVAKDLVVSLAYQVRTEDGVLVDESPVSAPLDYLHGHGSLISGLETAL

EGHEVGDKFDVAVGANDAYGQYDENLVQRVPKDVFMGVDELQVGMRFLA

ETDQGPVPVEITAVEDDHVVVDGNHMLAGQNLKFNVEVVAIREATEEEL

AHGHVHGAHDHHHDHDHDGGGSGGGSGGGSGGGSGGGSGGGGVQVETIS

PGDGRTFPKRGQTAVVHYTGMLEDGKKFDSSRDRNKPFKFMLGKQEVIR

GWEEGVAQMSVGQRAKLTISPDYAYGGGGSNKPTGYGSSSRRAPQTGGG

GSTLVFDVELLKLEGGGSRKHHHHHHHH.

The cells obtained from NMRI-mice immunized with the SlyD/FKBP12-IGF-1(74-90) fusion polypeptide were analyzed using an ELISA. Nunc Maxisorb F multi well plates were coated with SlyD/FKBP12-IGF-1(74-90), or SlyD/FKBP12-control (lacking the peptide of SEQ ID NO:5) by applying a solution comprising 0.41 µg polypeptide per ml. Thereafter free binding sites were blocked by applying a solution comprising 1% RPLA in PBS for one hour at room temperature. The wells were washed three times with a solution comprising 0.9% (w/v) sodium chloride and 0.05% (w/v) Tween. Chemically biotinylated IGF-1 (Peprotech, Human IGF-1, Cat.#100-11) and a biotinylated IGF-1 peptide loop comprising amino acids 3 to 15 of SEQ ID NO:5 respectively, was immobilized in the wells of StreptaWell High Bind SA multi well plates by applying a solution comprising 90 ng/ml of biotinylated IGF-1 or 500 ng/ml of biotinylated IGF-1-peptide loop, respectively. The loop peptide starts with a cysteine corresponding to position 2 of SEQ ID NO:5 and in addition contains a cysteine corresponding to position 16 of SEQ ID NO:5. These two cysteines have been used to cyclize the peptide, thereby forming a peptide loop. The N-terminal cysteine further has been used for biotinylation.

As samples the mouse sera diluted 1:50 with PBS were used. Optional further dilutions were performed in 1:4 steps until a final dilution of 1:819,200. The incubation time was one hour at room temperature. The wells were washed three times with a solution comprising 0.9% (w/v) sodium chloride and 0.05% (w/v) Tween. As detection antibody a polyclonal antibody against the constant domain of the target antibodies conjugated to a peroxidase was used (PAK<M-Fc□>S-F(ab')$_2$-POD). The detection antibody was applied at a concentration of 80 ng/ml in PBS comprising 1% (w/v) RSA. The incubation time was one hour at room temperature. The wells were washed three times with a solution comprising 0.9% (w/v) sodium chloride and 0.05% (w/v) Tween. Afterwards the wells were incubated with an ABTS solution for 15 minutes at room temperature. The intensity of the developed color was determined photometrically. Exemplary results are presented in the following Table.

TABLE

| mouse | IGF-1 | IGF-1-peptide loop | immobilized SlyD/FKBP12-IGF-1(74-90) | SlyD/FKBP12-control |
|---|---|---|---|---|
| K1575M1 | 189 | 194 | 2911 | 8379 |
| K1575M2 | 395 | 678 | 1470 | 2546 |
| K1575M3 | 465 | 272 | 4126 | 10091 |
| K1575M4 | 564 | — | 2426 | 6337 |
| K1576M1 | 2143 | 2058 | 8302 | 9934 |
| K1576M2 | — | — | 2960 | 8816 |
| K1576M3 | — | — | 2978 | 7756 |
| K1576M4 | — | — | 6957 | 11095 |
| K1576M5 | — | — | 11221 | 16588 |

—: no binding detectable in ELISA

Ten weeks after immunization antibody titers were determined by means of ELISA. Mice immunized with the SlyD/FKBP12-IGF-1(74-90) (SEQ ID NO:9) fusion polypeptide showed low titers versus IGF-1, versus the peptide of SEQ ID NO: 5, versus the SlyD/FKBP12-IGF-1(74-90) fusion polypeptide, and versus the SlyD/FKBP12 control polypeptide (SEQ ID NO:9 without the sequence of SEQ ID NO:5). Only one mouse provided for a sufficiently high anti-IGF-1 titer (K1576M1 in the above Table) and was used for the generation of hybridomas. No hybridomas could be identified producing antibodies specifically recognizing native IGF-1 in these experiments. SlyD/FKBP12-IGF-1 (74-90) seems not to be suitable as an immunization reagent for the development of IGF-1 specific antibodies. Later on, it was experimentally confirmed (data not shown), that the polypeptide SlyD/FKBP12-IGF-1(74-90) is not thermodynamically stable. Only the SlyD domain, but not the FKBP12-IGF-1(74-90) domain is correctly folded. Therefore, the fusion polypeptide does not effectively present the IGF-1(74-90) grafted sequence due to the marginal thermodynamic stability of the FKBP12 scaffold.

Example 3. Generation of Antibodies to Insulin-Like Growth Factor-1 Using a *Thermus thermophilus* SlyD-IGF-1(74-90) Fusion Polypeptide Antigen specific antibodies were eventually generated by immunization of mice with a chimeric *Thermus thermophilus*-SlyD-antigen fusion polypeptide. A plurality of epitopes can be targeted on this scaffold's surface, namely in the connecting region between FKBP domain and IF domain. The antibodies binding to the grafted target antigen can be identified by differential screening versus the wild-type *Thermus thermophilus*-SlyD as a negative control, or versus the native recombinant antigen (IGF-1) as a positive control. This example demonstrates the advantageous properties of the thermostable SlyD scaffold compared to the metastable human FKBP12, as described before. *Thermus thermophilus*-SlyD enables the presentation of enthalpic, rigid and stable structures and therefore is suitable to be used as a antigen-presenting scaffold for the development of monoclonal antibodies versus surrogate, native protein structures which would otherwise not be accessible to the immune system of e.g. an experimental animal.

3.1. Production of *Thermus thermophilus* SlyD Fusion Polypeptides

Guanidinium hydrochloride (GdmCl) (A-grade) was purchased from NIGU (Waldkraiburg, Germany). Complete® EDTA-free protease inhibitor tablets, imidazole and EDTA were from Roche Diagnostics GmbH (Mannheim, Germany), all other chemicals were analytical grade from Merck (Darmstadt, Germany). Ultrafiltration membranes (YM10, YM30) were purchased from Amicon (Danvers, Mass., USA), microdialysis membranes (VS/0.025 μm) and ultrafiltration units (Biomax ultrafree filter devices) were from Millipore (Bedford, Mass., USA). Cellulose nitrate and cellulose acetate membranes (1.2 μm, 0.45 μm and 0.2 μm pore size) for the filtration of crude lysates were from Sartorius (Goettingen, Germany).

Cloning of Expression Cassettes.

The sequence of the SlyD polypeptide from *Thermus thermophilus* was retrieved from the SwissProt database (acc. no. Q72H58). The sequence of the SlyD polypeptide from *Thermococcus gammatolerans* was retrieved from the Prosite database (acc. no. C5A738). Synthetic genes encoding *Thermus thermophilus* SlyD, *Thermus thermophilus* SlyD-IGF-1(74-90), and *Thermus thermophilus* SlyD-ΔIF were purchased from Sloning Biotechnology GmbH (Germany) and were cloned into a pQE80L expression vector. The codon usage was optimized for expression in *E. coli* host cells. Accordingly, analogous synthetic genes encoding *Thermococcus gammatolerans* SlyD, *Thermococcus gammatolerans* SlyD-IGF-2(53-65), *Thermus thermophilus* SlyD-IGF-1(74-90) antigen and *Thermococcus gammatolerans* SlyD-IGF-1(74-90) antigen were purchased from Geneart (Germany) and were cloned into pET24 expression vectors (Novagen, Madison, Wis., USA).

Additionally, a GS-linker (GGGS, SEQ ID NO:6) was included and a His-tag (SEQ ID NO:7) was fused to the carboxy terminal end in order to allow an affinity purification of the fusion polypeptides by means of immobilized metal ion affinity chromatography (IMAC).

In order to generate monoclonal antibodies specifically binding to the IGF-1-fragment 74-90 (amino acid sequence NKPTGYGSSSRRAPQTG, see SEQ ID NO:5) this amino acid sequence was grafted onto the molecular chaperone SlyD derived from *Thermus thermophilus* by molecular replacement of amino acids 71-122 (i.e. the IF domain) of the parent *Thermus thermophilus* SlyD protein. Due to an angle optimization of the IGF-1 insertion sequence, the aspartate residue at position 70 and the leucine residue at position 88 of the recombinant polypeptide were each substituted by a glycine (D70G and L88G). Thus the resulting fusion polypeptide has the amino acid sequence:

(SEQ ID NO: 10)
MRGSKVGQDKVVTIRYTLQVEGEVLDQGELSYLHGHRNLIPGLEEALEG

REEGEAFQAHVPAEKAYGPHGNKPTGYGSSSRRAPQTGGAGKDLDFQVE

VVKVREATPEELLHGHAHGGGSRKHHHHHHHH.

This *Thermus thermophilus*-SlyD-IGF-1 (74-90) fusion polypeptide (see FIG. 1 for SDS Page and Western blot) was used as an immunogen and also as a screening reagent for the development of anti-IGF-1 antibodies that are targeting the IGF-1 amino acid sequence (SEQ ID NO: 5)
NKPTGYGSSSRRAPQTG .

As one negative control, recombinant "wild-type" SlyD from *Thermus thermophilus* (SEQ ID NO:11) was used for screening purposes.

(SEQ ID NO: 11)
MKVGQDKVVTIRYTLQVEGEVLDQGELSYLHGHRNLIPGLEEALEGRE

EGEAFQAHVPAEKAYGPHDPEGVQVVPLSAFPEDAEVVPGAQFYAQDM

EGNPMPLTVVAVEGEEVTVDFNHFLAGKDLDFQVEVVKVREATPEELL

HGHAHGGGSRKHHHHHH .

In addition, a *Thermus thermophilus* SlyD-ΔIF fusion polypeptide (SEQ ID NO:12) was produced for screening and specificity testing. This *Thermus thermophilus* SlyD-ΔIF fusion polypeptide lacks the IF domain, which was replaced by the amino acid sequence motif AGSGSS, and comprises a C-terminal amino acid sequence tag of SEQ ID NO:7.

(SEQ ID NO: 12)
MRGSKVGQDKVVTIRYTLQVEGEVLDQGELSYLHGHRNLIPGLEEAL

EGREEGEAFQAHVPAEKAYGPHGAGSGSSGAGKDLDFQVEVVKVREA

TPEELLHGHAHGGGSRKHHHHHHHH .

As a further control the native SlyD from *Thermococcus gammatolerans* comprising a C-terminal amino acid sequence tag of SEQ ID NO:7 was used:

(SEQ ID NO: 13)
MKVERGDFVLFNYVGRYENGEVFDTSYESVAREQGIFVEEREYSPIGV

TVGAGEIIPGIEEALLGMELGEKKEVVVPPEKGYGMPREDLIVPVPIE

QFTSAGLEPVEGMYVMTDAGIAKILKVEEKTVRLDFNHPLAGKTAIFE

IEVVEIKKAGEAGGGSRKHHHHHH .

In order to assess for cross reactivity against IGF-2 the structurally homologous sequence from human IGF-2 (amino acids 53-65) was inserted into *Thermococcus gammatolerans* SlyD, which was fused with a GS-spacer and a hexahistidine-tag (for purification and refolding) at the C-terminus:

(SEQ ID NO: 14)
MKVERGDFVLFNYVGRYENGEVFDTSYESVAREQGIFVEEREYSPIGV

TVGAGEIIPGIEEALLGMELGEKKEVVVPPEKGYGMP-G-SRVSRRSR

G-G-AGKTAIFEIEVVEIKKAGEAGGGSRKHHHHHH .

Expression, Purification and Refolding of Fusion Polypeptides.

All SlyD polypeptides can be purified and refolded by using almost identical protocols. *E. coli* BL21 (DE3) cells harboring the particular expression plasmid were grown at 37° C. in LB medium containing the respective antibiotic for selective growth (Kanamycin 30 µg/ml, or Ampicillin (100 µg/ml)) to an OD600 of 1.5, and cytosolic overexpression was induced by adding 1 mM isopropyl-ß-D-thiogalactoside (IPTG). Three hours after induction, cells were harvested by centrifugation (20 min at 5,000 g), frozen and stored at −20° C. For cell lysis, the frozen pellet was resuspended in chilled 50 mM sodium phosphate buffer (pH 8.0) supplemented with 7 M GdmCl and 5 mM imidazole. Thereafter the suspension was stirred for 2-10 hours on ice to complete cell lysis. After centrifugation (25,000 g, 1 h) and filtration (cellulose nitrate membrane, 8.0 µm, 1.2 µm, 0.2 µm), the lysate was applied onto a Ni-NTA column equilibrated with the lysis buffer. In the subsequent washing step the imidazole concentration was raised to 10 mM (in 50 mM sodium phosphate buffer (pH 8.0) comprising 7 M GdmCl) and 5 mM TCEP was added in order to keep the thiol moieties in a reduced form and to prevent premature disulfide bridging. At least 15 to 20 volumes of the reducing washing buffer were applied. Thereafter, the GdmCl solution was replaced by 50 mM sodium phosphate buffer (pH 8.0) comprising 100 mM NaCl, 10 mM imidazole, and 5 mM TCEP to induce conformational refolding of the matrix-bound SlyD fusion polypeptide. In order to avoid reactivation of co-purifying proteases, a protease inhibitor cocktail (Complete® EDTA-free, Roche) was added to the refolding buffer. A total of 15 to 20 column volumes of refolding buffer were applied in an overnight procedure. Thereafter, both TCEP and the Complete® EDTA-free inhibitor cocktail were removed by washing with 10 column volumes 50 mM sodium phosphate buffer (pH 8.0) comprising 100 mM NaCl and 10 mM imidazole. In the last washing step, the imidazole concentration was raised to 30 mM (10 column volumes) in order to remove tenacious contaminants. The refolded polypeptide was then eluted by applying 250 mM imidazole in the same buffer. Protein-containing fractions were assessed for purity by Tricine-SDS-PAGE (Schaegger, H. and von Jagow, G., Anal. Biochem. 166 (1987) 368-379) and pooled. Subsequently, the protein was subjected to size-exclusion-chromatography (Superdex™ HiLoad, Amersham Pharmacia) using potassium phosphate as the buffer system (50 mM potassium phosphate buffer (pH 7.0), 100 mM KCl, 0.5 mM EDTA). Finally, the protein-containing fractions were pooled and concentrated in an Amicon cell (YM10) to a concentration of ~5 mg/ml.

Figure 2:
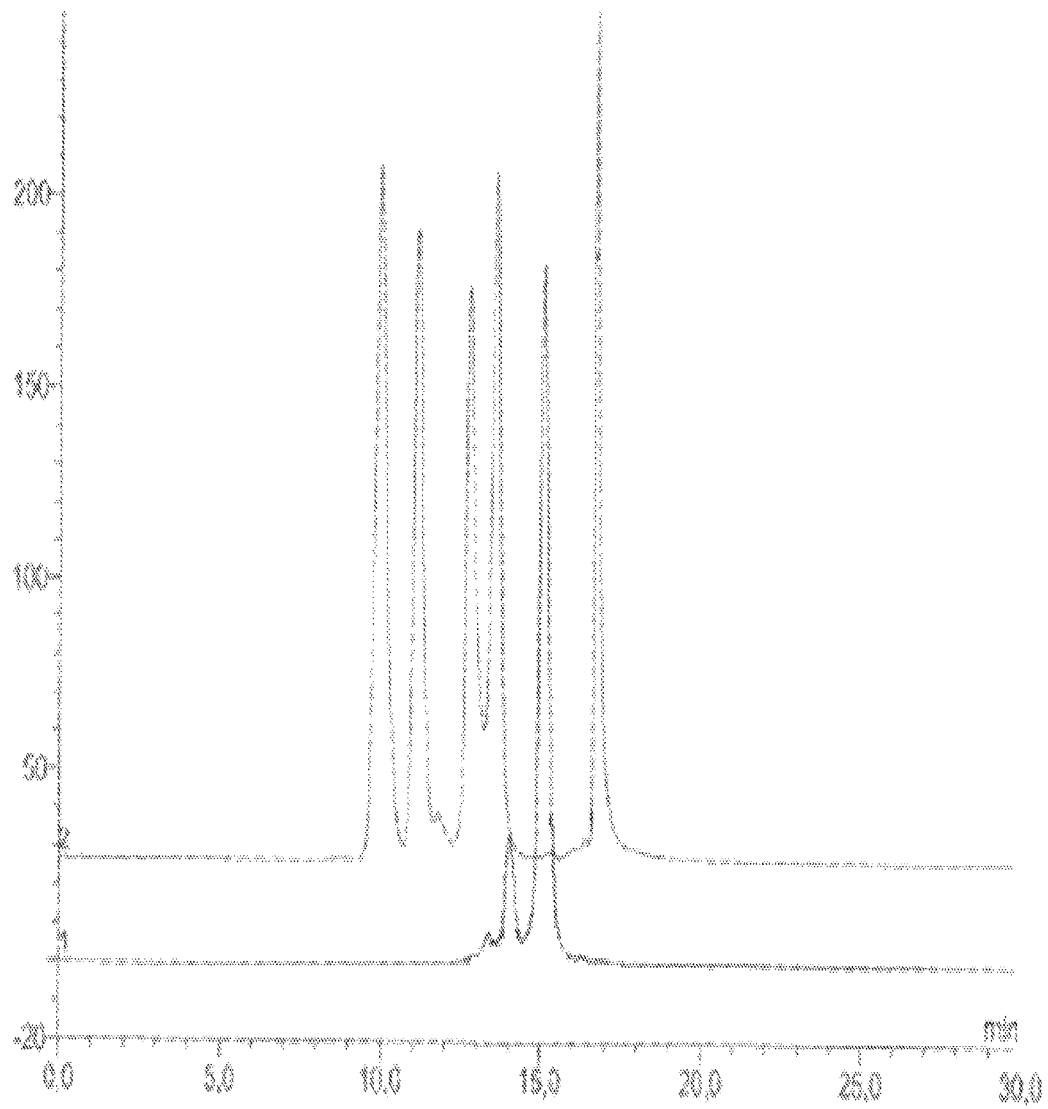
FIG. 2 presents an analytical HPLC chromatogram of *Thermus thermophilus* SlyD-IGF-1(74-90) fusion polypeptide (Upper line: molecular weight standards. Lower line: fusion polypeptide).
Figure 5A:
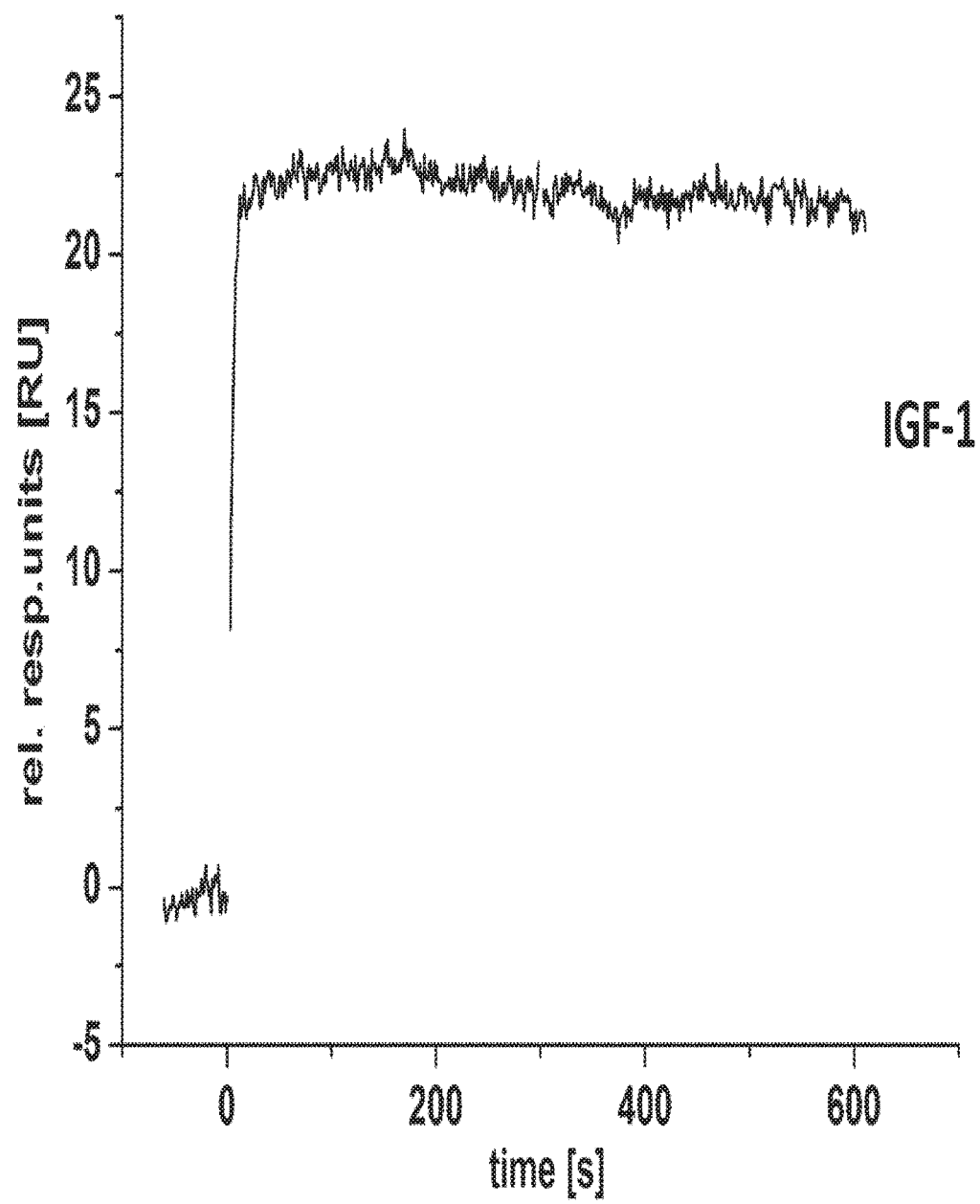
FIG. 5A presents an exemplary BIAcore kinetic screening of primary culture <IGF-1>M-11.0.15 versus IGF-1 polypeptide (the primary culture is designated 11.0.15, whereas after final cloning the denomination is 11.10.15).
Figure 5B:
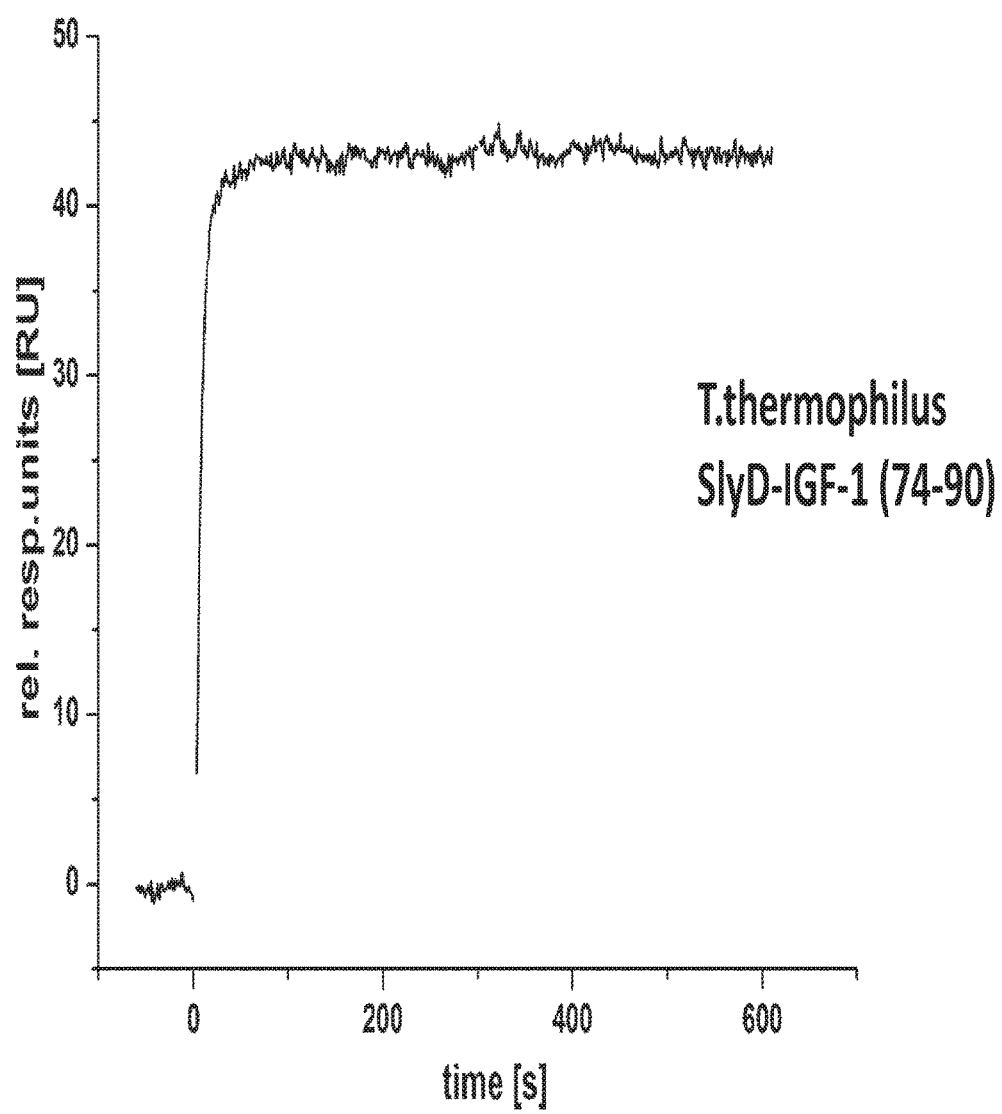
FIG. 5B presents an exemplary BIAcore kinetic screening of primary culture <IGF-1>M-11.0.15 versus *Thermus thermophilus* SlyD-IGF-1(74-90) fusion polypeptide (the primary culture is designated 11.0.15, whereas after final cloning the denomination is 11.10.15).
Figure 5C:
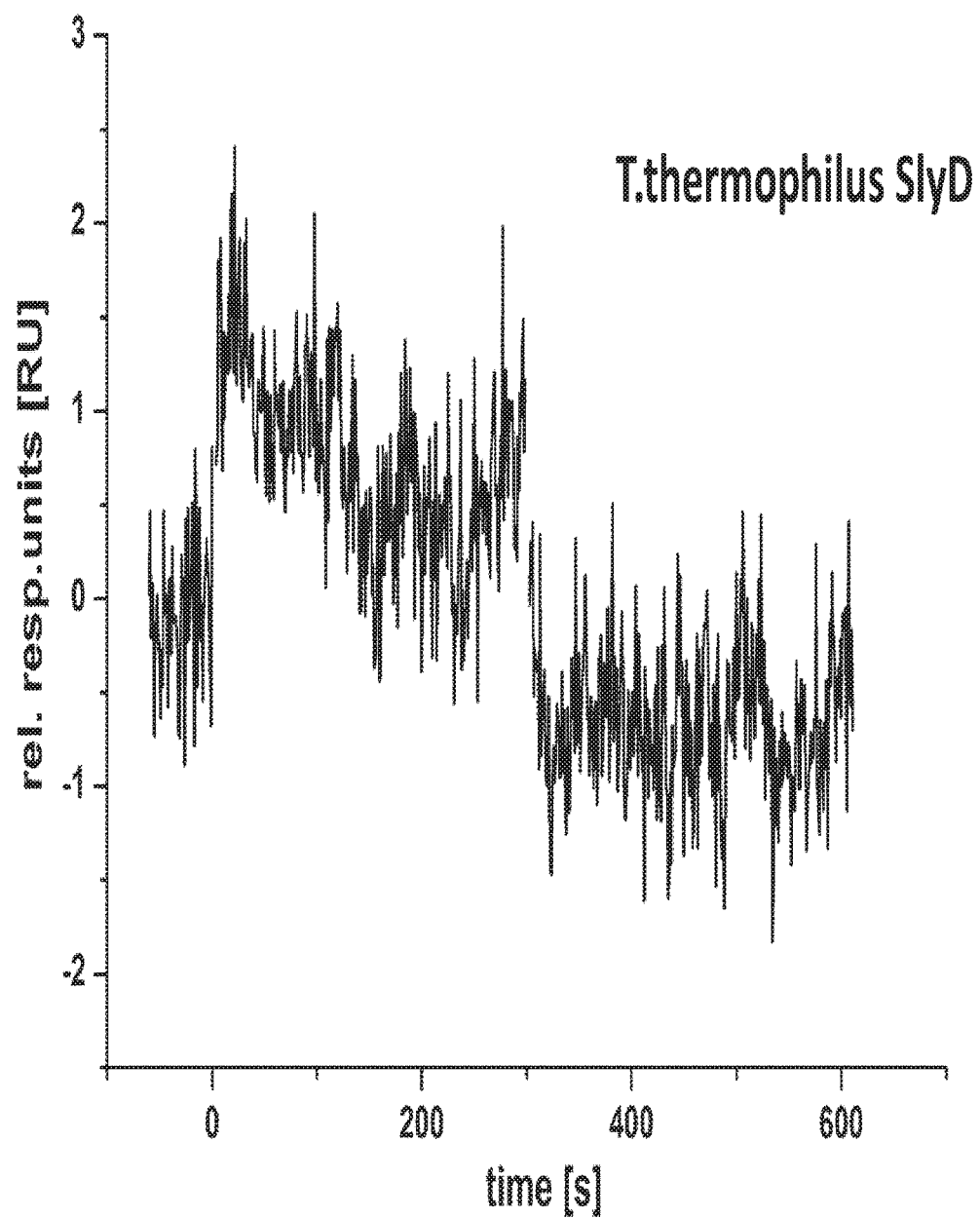
FIG. 5C presents an exemplary BIAcore kinetic screening of primary culture <IGF-1>M-11.0.15 versus *Thermus thermophilus* wild type SlyD polypeptide (the primary culture is designated 11.0.15, whereas after final cloning the denomination is 11.10.15).
Figure 5D:
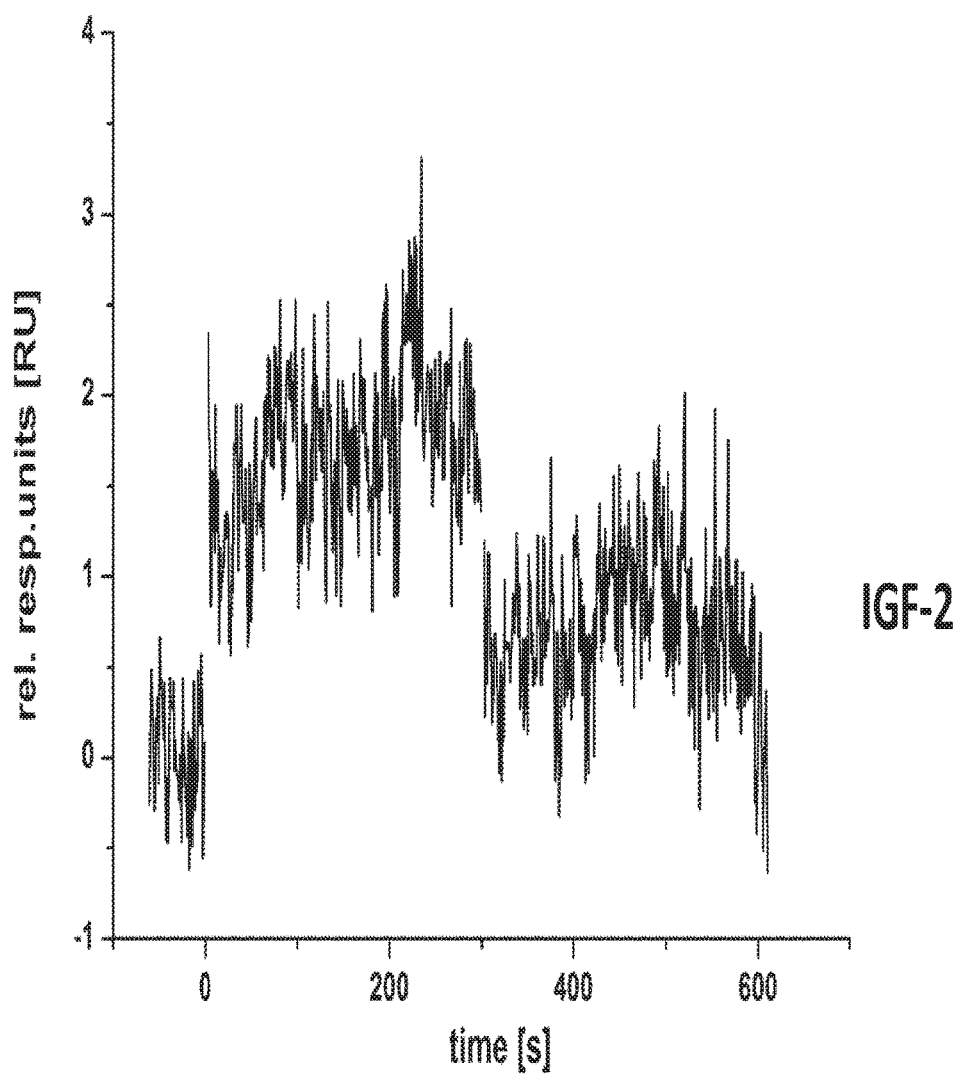
FIG. 5D presents an exemplary BIAcore kinetic screening of primary culture <IGF-1>M-11.0.15 versus IGF-2 polypeptide (the primary culture is designated 11.0.15, whereas after final cloning the denomination is 11.10.15).
Figure 7A:
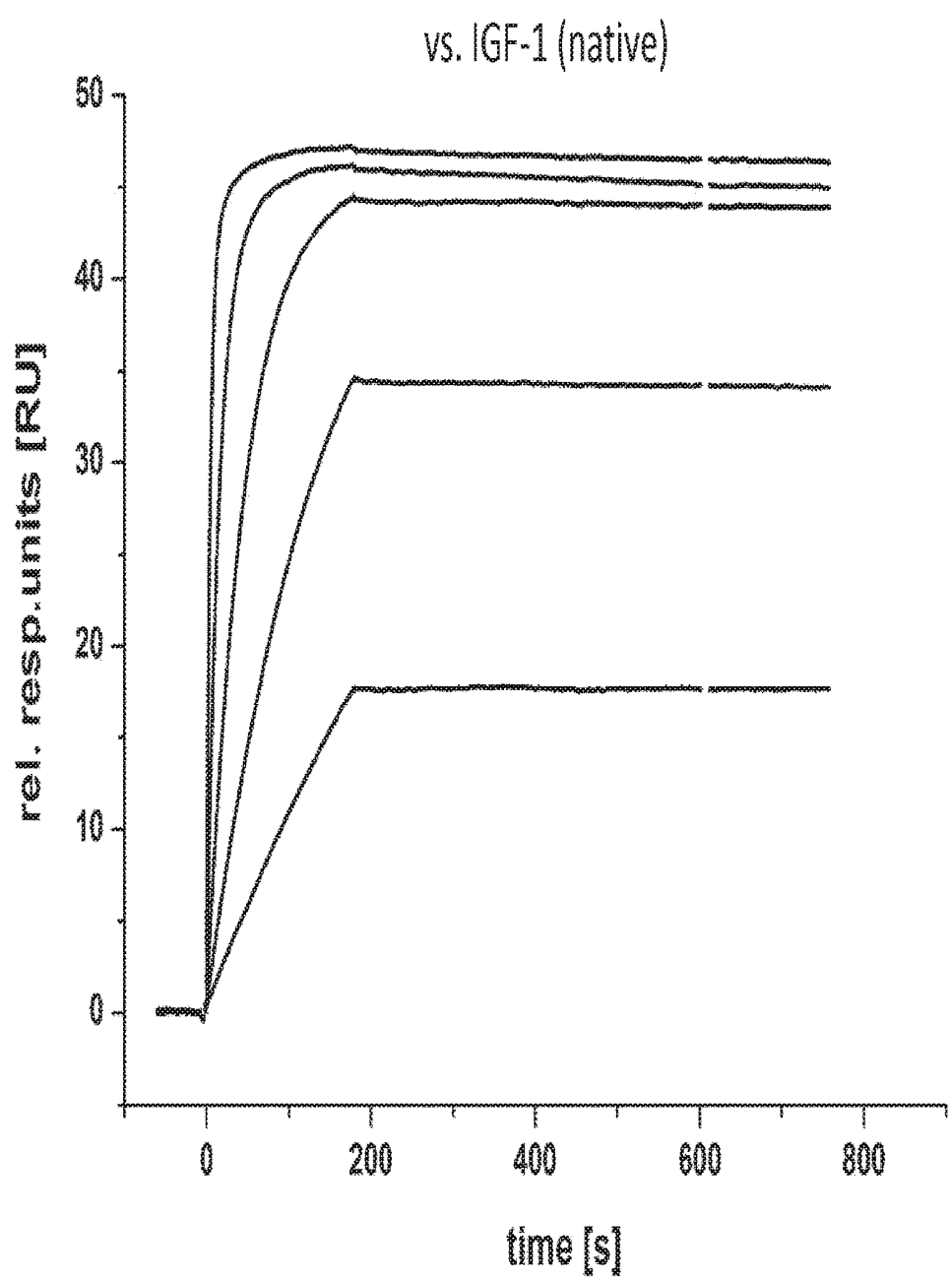
FIG. 7A presents BIAcore measurements of <IGF-1>M-11.11.17-IgG versus IGF-1, IGF-2, *Thermus thermophilus* SlyD-IGF-1(74-90) fusion polypeptide, *Thermus thermophilus* wild type SlyD polypeptide, *Thermococcus gammatolerans* wild-type SlyD polypeptide *Thermus thermophilus* SlyD-ΔIF fusion polypeptide, and *Thermococcus gammatolerans* SlyD-IGF-2(53-65) fusion polypeptide.
Figure 7E:
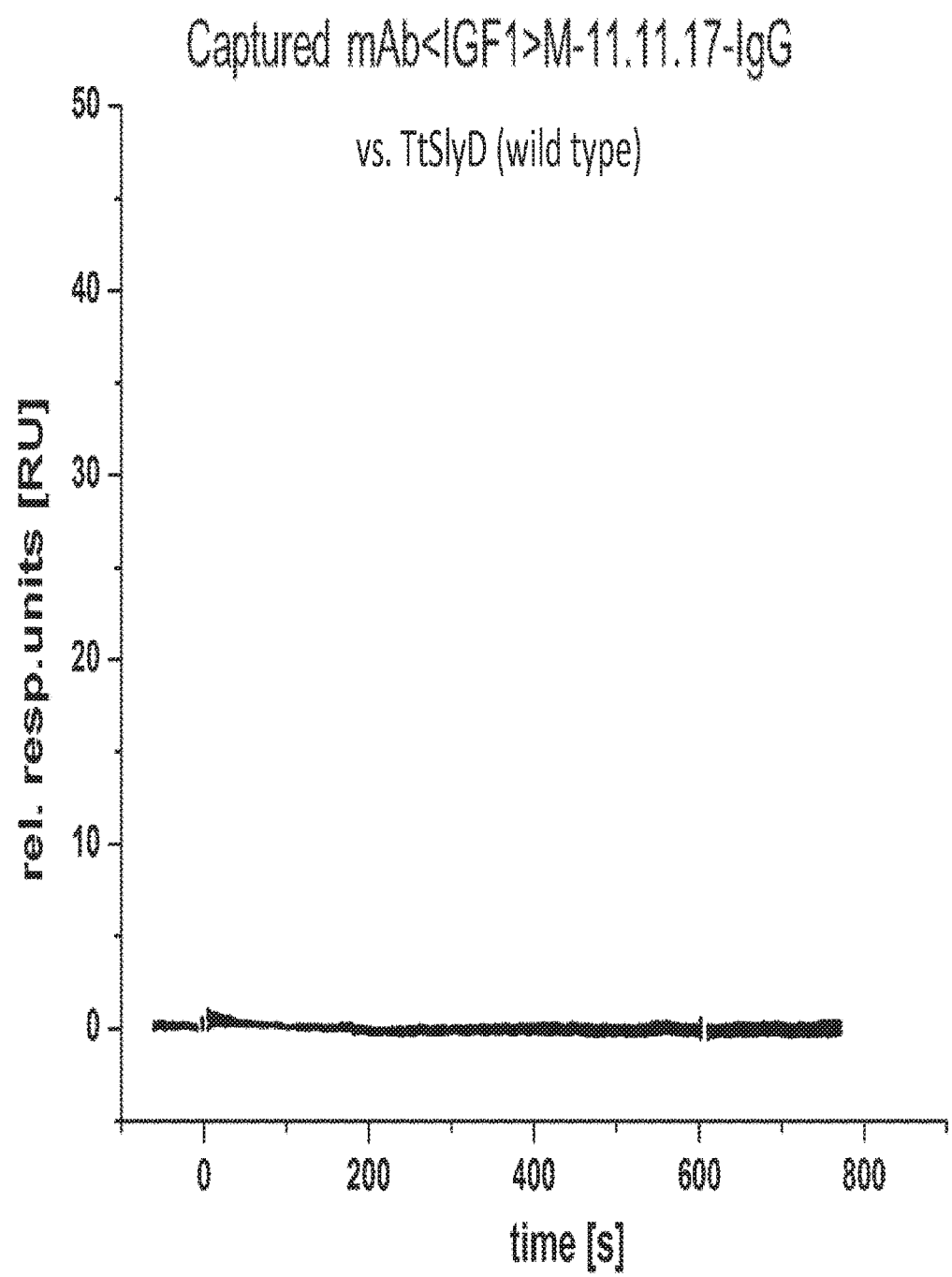
FIG. 7E presents BIAcore measurements of <IGF-1>M-11.11.17-IgG versus *Thermus thermophilus* wild type SlyD polypeptide.

The *Thermus thermophilus* SlyD-IGF-1(74-90) fusion polypeptide (SEQ ID NO:10) could be purified successfully as a soluble and stable polypeptide in a monomeric form (see FIG. 2).

UV Spectroscopic Measurements.

Protein concentration measurements were performed with an UVIKON XL double-beam spectrophotometer. The molar extinction coefficients ($\square$280) for the SlyD variants were calculated according to Pace (Pace, C. N., et al., Protein Sci. 4 (1995) 2411-2423).

CD Spectroscopic Measurements.

To examine whether the chimeric fusion proteins according to the disclosure adopt a folded conformation CD spectra in the near-UV region were measured. CD spectra were recorded and evaluated using a JASCO J-720 instrument and JASCO software according to the manufacturer's recommendations. A quartz cuvette with 0.2 cm pathlength was used. The instrument parameters were set to 1° C. resolution, 1 nm band width and a sensitivity of 5 mdeg. The sample buffer was 50 mM potassium phosphate pH 7.5, 100 mM NaCl, 1 mM EDTA. The protein concentration for each analysis was 36 µM (for *Thermus thermophilus* wild-type SlyD), 23 µM (for *Thermus thermophilus* SlyD-ΔIF), 16 µM (for *Thermus thermophilus* SlyD-antigen), 19 μM (for *Thermococcus gammadurans* wild-type SlyD), and 16 μM (for *Thermococcus gammadurans* SlyD-antigen). CD signals were recorded at 20° C. between 250 nm and 330 nm with 0.5 nm resolution and with a scan speed of 20 nm per minute. In order to improve the signal-to-noise ratio, the spectra were accumulated (9-times). In a subsequent experimental embodiment the CD signals were recorded as a function of temperature at a fixed wavelength. Melting and refolding curves (20° C.-100° C.//100° C.-20° C.) were recorded for the *Thermococcus gammatolerans* SlyD derivatives as well as for the *Thermus thermophilus* SlyD derivatives (20° C.-85° C.//85° C.-20° C.) at 277 nm. The heating and the cooling rate was 1° C. per minute.

CD spectra of the fusion polypeptides *Thermus thermophilus* wild-type SlyD, *Thermus thermophilus* SlyD-ΔIF and *Thermus thermophilus* SlyD with grafted antigen insert have been recorded. The near-UV CD signatures unambiguously showed that at 20° C. all fusion polypeptides are folded into compact, presumably native-like conformation, even when the IF domain is missing or is being replaced by an heterologous amino acid (antigen) graft.

After a heating/cooling cycle, i.e. after thermally induced unfolding and subsequent cooling of the protein sample, the near UV CD spectrum of *Thermus thermophilus* SlyD with the grafted antigen is essentially restored. That is, the near UV CD spectrum of *Thermus thermophilus* SlyD after melting and refolding is virtually identical with the spectrum of the native molecule. This is strongly indicative that thermally induced unfolding of *Thermus thermophilus* SlyD with the antigen insert is fully reversible. High intrinsic thermodynamic stability in combination with reversibility of unfolding are highly desired features of an immunogen.

As for *Thermococcus gammatolerans* SlyD-antigen polypeptide, thermally induced unfolding was not complete even at 100° C. In other words, even at the boiling point of water, which constitutes the accessible temperature limit in our experimental setup, a significant portion of the scaffold/graft molecules retain their native-like fold. Thus, the extraordinary stability of FKBP domains from thermophilic organisms enables the grafting of polypeptides by replacement of the respective IF domains while at the same time the overall fold of the newly generated chimeric scaffold protein is largely retained. In brief, thermostable FKBP domains serve a role as a molecular clamp into which the immunogen peptide may be fixed in a well-defined conformation.

3.2. Immunization of Mice with *Thermus hermophiles* SlyD-IGF-1(74-90) and Development of Monoclonal Antibodies Versus IGF-1

8-12 weeks old Balb/c and NMRI mice, respectively, were subjected to repeated intraperitoneal immunizations with 100 μg of *Thermus hermophiles* SlyD-IGF-1(74-90). The mice were immunized three times, i.e. also at the time points of 6 weeks and 10 weeks after the initial immunization. The first immunization can be performed using complete Freund's adjuvant, the second and third immunizations were done using incomplete Freund's adjuvant. The mice serum titers versus native recombinant IGF-1 and *Thermus hermophiles* SlyD-IGF-1(74-90) were tested after 12 weeks by ELISA methods as described in the following. The ELISA was performed on a Tecan Sunrise running under Firmware: V 3.15 19 Mar. 1; XREAD PLUS Version: V 4.20. Nunc Maxisorb F multi well plates were coated with *Thermus hermophiles* SlyD-IGF-1(74-90) by applying a solution comprising 0.5 μg polypeptide per ml. The isolated and biotinylated IGF-1 was immobilized in the wells of StreptaWell High Bind SA multi well plates by applying a solution comprising 90 ng/ml biotinylated IGF-1. Thereafter free binding sites were blocked by applying a solution comprising 1% RPLA in PBS for one hour at room temperature. The wells were washed three times with a solution comprising 0.9% (w/v) sodium chloride and 0.05% (w/v) Tween. Mouse serum was diluted 1:50 with PBS and used as sample. Optional further dilution was performed in 1:4 steps until a final dilution of 1:819,200. The incubation time was one hour at room temperature. The wells were washed three times with a solution comprising 0.9% (w/v) sodium chloride and 0.05% (w/v) Tween. As detection antibody a polyclonal antibody against the constant domain of the target antibodies conjugated to a peroxidase was used (PAK<M-Fc□>S-F(ab')$_2$-POD). The detection antibody was applied at a concentration of 80 ng/ml in PBS comprising 1% (w/v) RSA. The incubation time was one hour at room temperature. The wells were washed three times with a solution comprising 0.9% (w/v) sodium chloride and 0.05% (w/v) Tween. Afterwards the wells were incubated with an ABTS solution for 15 minutes at room temperature. The intensity of the developed color was photometrically determined. FIG. 3 shows mice serum titers obtained.

Three days before preparation of spleen cells and fusion with a myeloma cell line, the final booster immunization was performed by i.v. injection of 100 μg of *Thermus hermophiles* SlyD-IGF-1(74-90) fusion polypeptide.

ELISA Screening.

Primary culture supernatants were tested by ELISA for reactivity against the immunogen *Thermus thermophilus* SlyD-IGF-1(74-90), biotinylated native IGF-1 and wild-type *Thermus thermophilus* SlyD and a blank plate, respectively. ELISA was driven with a Tecan SUNRISE, Firmware: V 3.15 19 Mar. 1; XREAD PLUS Version: V 4.20. Nunc Maxisorb F multi well ELISA plates were coated with 5 μg/ml SlyD-fusion polypeptides. StreptaWell High Bind SA multi well plates were coated with 125 ng/ml recombinant biotinylated IGF-1 antigen. Thereafter free binding sites were blocked by 1% RPLA in PBS for one hour at room temperature. The wells were washed three times with a solution comprising 0.9% (w/v) sodium chloride and 0.05% (w/v) Tween. Undiluted hybridoma supernatants in RPMI 1640 medium were used as samples. The incubation time was one hour at room temperature. The wells were washed three times with a solution comprising 0.9% (w/v) sodium chloride and 0.05% (w/v) Tween. As detection antibody a polyclonal antibody against the constant domain of the target antibodies conjugated to a peroxidase was used (PAK<M-Fc□>S-F(ab')$_2$-POD). The detection antibody was applied at a concentration of 80 ng/ml in PBS comprising 1% (w/v) RSA. The incubation time was one hour at room temperature. The wells were washed three times with a solution comprising 0.9% (w/v) sodium chloride and 0.05% (w/v) Tween. Afterwards the wells were incubated with an ABTS solution for 15 minutes at room temperature. The intensity of the developed color was determined photometrically at 405 nm. The reference wavelength was 492 nm (see FIG. 4). Primary hybridoma supernatants, showing fast and strong color formation in ELISA upon binding to recombinant IGF-1, *Thermus thermophilus* SlyD-IGF-1(74-90) and less binding to *Thermus thermophilus* SlyD were transferred into the kinetic screening process as described in the following.

SPR-Based Kinetic Screening.

*Thermus thermophilus* SlyD-IGF-1(74-90), native recombinant IGF-1, native recombinant IGF-2, wild-type *Thermus thermophilus* SlyD, and *Thermus thermophilus*-SlyD-IGF-1(74-90) were used in an SPR-based kinetic screening analysis. For SPR analyses it is generally accepted to use monomeric and monovalent analytes in solution to determine the antibody binding kinetics according to a Langmuir model. Furthermore, it is rather advantageous for SPR measurements to use an analyte with higher molecular weight to increase the sensitivity of the measurements, since SPR is a mass sensitive analysis.

The kinetic screening was performed on a BIAcore A100 instrument under control of the software version V1.1. A BIAcore CM5 chip was mounted into the instrument and was hydrodynamically addressed and preconditioned according to the manufacturer's instructions. As a running buffer an HBS-EP buffer was used (10 mM HEPES (pH 7.4), 150 mM NaCl, 1 mM EDTA, 0.05% (w/v) P20). A polyclonal rabbit anti-mouse IgG Fc capture antibody is immobilized at 30 µg/ml in 10 mM sodium acetate buffer (pH 4.5) to spots 1, 2, 4 and 5 in flow cells 1, 2, 3 and 4 at 10,000 RU (FIGS. 5A-D). The antibody was covalently immobilized via NHS/EDC chemistry. The sensor was deactivated thereafter with a 1 M ethanolamine solution. Spots 1 and 5 were used for the determination and spots 2 and 4 were used as reference spots. Prior to application to the sensor chip the hybridoma supernatants were diluted 1:2 in HBS-EP buffer. The diluted solution was injected at a flow rate of 30 µl/min for 1 min. Immediately thereafter the analyte, such as the Thermus thermophilus SlyD-IGF-1(74-90), fusion polypeptide, was injected at a flow rate of 30 µl/min for 2 min. Thereafter the signal was recorded for 5 min. dissociation time. The sensor was regenerated by injecting a 10 mM glycine-HCl solution (pH 1.7) for 2 min at a flow rate of 30 µl/min. Two report points, the recorded signal shortly before the end of the analyte injection, denoted as binding late (BL) and the recorded signal shortly before the end of the dissociation time, stability late (SL), were used to characterize the Kinetic Screening performance.

Furthermore, the dissociation rate constant $k_d$ (1/s) was calculated according to a Langmuir model and the antibody/antigen complex half-life was calculated in minutes according to the formula $\ln(2)/(60*kd)$.

As can be seen, monoclonal antibodies were obtained by immunization with the antigen Thermus thermophilus SlyD-IGF-1(74-90), and screening with Thermus thermophilus SlyD-IGF-1(74-90), Thermus thermophilus SlyD "wild-type", native IGF-1 and native IGF-2. The scaffold-based screening approach allows to specifically develop antibodies binding to the IGF-1, epitopes comprised in SEQ ID NO: 5.

The primary culture supernatants were further developed by limited dilution into clone culture supernatants by methods known in the art. The clone culture supernatants were tested in a functional assay for affinity and specificity.

The clonal cultures were analyzed by means of ELISA for specific binding to IGF-1 in comparison to binding to Thermus thermophilus-SlyD-IGF-1 (74-90) and Thermus thermophilus-SlyD, respectively (see FIG. 6).

3.3. BIAcore Characterization of Antibody Producing Clone Culture Supernatants

A BIAcore T200 instrument (GE Healthcare) was used with a BIAcore CM5 sensor mounted into the system. The sensor was preconditioned by a 1 min. injection at 100 µl/min of 0.1% SDS, 50 mM NaOH, 10 mM HCl and 100 mM $H_3PO_4$.

The system buffer was PBS-DT (10 mM $Na_2HPO_4$, 0.1 mM $KH_2PO_4$, 2.7 mM KCl, 137 mM NaCl, 0.05% Tween® 20, 5% DMSO). The sample buffer was the system buffer.

The BIAcore T200 System was driven under the control software V1.1.1. Polyclonal rabbit IgG antibody <IgGFCγM>R (Jackson ImmunoResearch Laboratories Inc.) was immobilized at 30 µg/ml in 10 mM sodium acetate buffer (pH 4.5) at 6500 RU on the flow cells 1, 2, 3, and 4, respectively, via EDC/NHS chemistry according to the manufacturer's instructions. Finally, the sensor surface was blocked with a 1 M ethanolamine solution. The complete experiment was performed at 25° C.

The clone culture supernatants containing the respective antibodies at approx. 40 nM were captured for 2 min at a flow rate of 5 µl/min on the <IgGFCγM>R surface. As analytes in solution the recombinant native IGF-1 (Peprotech Inc. Cat.#100-11), recombinant native IGF-2 (Peprotech Inc. Cat.#100-12), Thermus thermophilus SlyD-IGF-1 (74-90), recombinant wild-type Thermus thermophilus SlyD, recombinant Thermus thermophilus SlyD-ΔIF, recombinant wild-type Thermococcus gammadurans SlyD, recombinant Thermococcus gammadurans SlyD-IGF-2 (53-65) fusion polypeptides were used. Thermus thermophilus SlyD-ΔIF is solely the FKBP domain of Thermus thermophilus SlyD lacking the IF domain. Thermococcus gammadurans SlyD-IGF-2(53-65) was used to counterscreen and investigate the specificity for the IGF-1 hairpin in contrast to the IGF-2 hairpin insertion. The respective analytes were injected at different concentration steps from 90 nM, 30 nM, 10 nM, 3.3 nM, 1.1 nM and 0 nM. The association phase was monitored for 3 min. at a flow rate of 100 µl/min. The dissociation was monitored for 10 min. at a flow rate of 100 µl/min. The system was regenerated using a 10 mM glycine buffer (pH 1.7). Kinetics were evaluated using the BIAcore Evaluation Software.

The following terms are used herein: mAb: monoclonal antibody; RU: Relative response unit of monoclonal antibody captured on the sensor; Antigen: antigen in solution; kDa: molecular weight of the antigens in kilo Dalton injected as analytes in solution; ka: association rate constant; kd: dissociation rate constant; t½ diss: antibody-antigen complex half-life calculated according to the formula t½ diss=ln(2)/60*kd; KD: dissociation constant; $R_{MAX}$: Binding signal at the end of the association phase of the 90 nM analyte injection; MR: Molar Ratio; $Chi^2$: failure of the measurement; n.d.: not detectable.

In FIGS. 7A-G exemplary BIAcore measurements with the anti-IGF-1 monoclonal antibody mAb<IGF1>M-11.11.17, which was obtained from the Thermus thermophilus-SlyD-IGF-1 (74-90) fusion polypeptide immunization campaign, are shown. The antibodies specifically bind the Thermus thermophilus-SlyD-IGF-1 (74-90) fusion polypeptide and IGF-1 but do not bind to all the other polypeptides tested.

Another hybridoma cell line producing the monoclonal antibody mAb<IGF1>M-11.09.15 was obtained in an analogous manner.

FIG. 8 shows that the scaffold-derived monoclonal antibody M-11.11.17 has picomolar affinity versus IGF-1. The scaffold-derived monoclonal antibody M-10.7.9 has nanomolar affinity versus IGF-1. No cross-reactivity versus IGF-2, nor versus wild-type Thermus thermophilus SlyD, nor versus wild-type Thermococcus gammatolerans SlyD, nor versus Thermus thermophilus SlyD-ΔIF fusion polypeptide, nor versus Thermococcus gammatolerans SlyD-IGF-2(53-65) fusion polypeptide was detectable.

M-2.28.44 is a monoclonal antibody obtained by conventional immunization of mice with recombinant human IGF-1. Despite the fact that the antibody shows a 30 pM affinity versus IGF-1, a 500 pM cross reactivity was found versus IGF-2 see also FIG. 8). Since both Thermus thermophilus SlyD-IGF-1(74-90) and Thermococcus gammatolerans SlyD-IGF-2 (53-65) are not bound by this monoclonal antibody, it can be concluded that the cross-reacting IGF-2 epitope is not the IGF hairpin region.

3.3. Epitope Analysis for <IGF-1> Monoclonal Antibodies

CelluSpots™ Synthesis and Epitope Mapping.

Epitope mappings were carried out by means of a library of overlapping, immobilized peptide fragments (length: 15 amino acids) corresponding to the sequence of human IGF1. Each peptide synthesized was shifted by one amino acid, i.e. it had 14 amino acids overlap with the previous and the following peptide, respectively. For preparation of the peptide arrays the Intavis CelluSpots™ technology was employed. In this approach, peptides are synthesized with an automated synthesizer (Intavis MultiPep RS) on modified cellulose disks which are dissolved after synthesis. The solutions of individual peptides covalently linked to macromolecular cellulose are then spotted onto coated microscope slides. The CelluSpots™ synthesis was carried out stepwise utilizing 9-fluorenylmethoxycarbonyl (Fmoc) chemistry on amino-modified cellulose disks in a 384-well synthesis plate. In each coupling cycle, the corresponding amino acids were activated with a solution of DIC/HOBt in DMF. Between coupling steps un-reacted amino groups were capped with a mixture of acetic anhydride, diisopropylethyl amine and 1-hydroxybenzotriazole. Upon completion of the synthesis, the cellulose disks were transferred to a 96-well plate and treated with a mixture of trifluoroacetic acid (TFA), dichloromethane, triisoproylsilane (TIS) and water for side chain deprotection. After removal of the cleavage solution, the cellulose bound peptides are dissolved with a mixture of TFA, TFMSA, TIS and water, precipitated with diisopropyl ether and re-suspended in DMSO. The peptide solutions were subsequently spotted onto Intavis CelluSpots™ slides using an Intavis slide spotting robot.

For epitope analysis, the slides prepared as described above were washed with ethanol and then with Tris-buffered saline (TBS; 50 mM Tris, 137 mM NaCl, 2.7 mM KCl, pH 8) before blocking for 16 h at 4° C. with 5 mL 10× Western Blocking Reagent (Roche Applied Science), 2.5 g sucrose in TBS, 0.1% Tween 20. The slide was washed with TBS and 0.1% Tween 20 and incubated afterward with 1 □g/mL of the corresponding IGF1 antibodies in TBS and 0.1% Tween 20 at ambient temperature for 2 h and subsequently washed with TBS+0.1% Tween 20. For detection, the slide was incubated with anti-rabbit/anti-mouse secondary HRP-antibody (1:20000 in TBS-T) followed by incubation with chemiluminescence substrate luminol and visualized with a LumiImager (Roche Applied Science). ELISA-positive SPOTs were quantified and through assignment of the corresponding peptide sequences the antibody binding epitopes were identified.

Sequences used for epitope mapping (for the sake of convenience only the first 32 are given, yet the full IGF-1 molecule has been scanned):

| SEQ ID NO | Sequence |
|---|---|
| 33 | A-L-Q-F-V-C-G-D-R-G-F-Y-F-G-N |
| 34 | L-Q-F-V-C-G-D-R-G-F-Y-F-G-N-K |
| 35 | Q-F-V-C-G-D-R-G-F-Y-F-G-N-K-P |
| 36 | F-V-C-G-D-R-G-F-Y-F-G-N-K-P-T |
| 37 | V-C-G-D-R-G-F-Y-F-G-N-K-P-T-G |
| 38 | C-G-D-R-G-F-Y-F-G-N-K-P-T-G-Y |
| 39 | G-D-R-G-F-Y-F-G-N-K-P-T-G-Y-G |
| 40 | D-R-G-F-Y-F-G-N-K-P-T-G-Y-G-S |
| 41 | R-G-F-Y-F-G-N-K-P-T-G-Y-G-S-S |
| 42 | G-F-Y-F-G-N-K-P-T-G-Y-G-S-S-S |
| 43 | F-Y-F-G-N-K-P-T-G-Y-G-S-S-S-R |
| 44 | Y-F-G-N-K-P-T-G-Y-G-S-S-S-R-R |
| 45 | F-G-N-K-P-T-G-Y-G-S-S-S-R-R-A |
| 46 | G-N-K-P-T-G-Y-G-S-S-S-R-R-A-P |
| 47 | N-K-P-T-G-Y-G-S-S-S-R-R-A-P-Q |
| 48 | K-P-T-G-Y-G-S-S-S-R-R-A-P-Q-T |
| 49 | P-T-G-Y-G-S-S-S-R-R-A-P-Q-T-G |
| 50 | T-G-Y-G-S-S-S-R-R-A-P-Q-T-G-G |
| 51 | G-Y-G-S-S-S-R-R-A-P-Q-T-G-G-I |
| 52 | Y-G-S-S-S-R-R-A-P-Q-T-G-G-I-V |
| 53 | G-S-S-S-R-R-A-P-Q-T-G-G-I-V-D |
| 54 | S-S-S-R-R-A-P-Q-T-G-G-I-V-D-E |
| 55 | S-S-R-R-A-P-Q-T-G-G-I-V-D-E-C |
| 56 | S-R-R-A-P-Q-T-G-G-I-V-D-E-C-C |
| 57 | R-R-A-P-Q-T-G-G-I-V-D-E-C-C-F |
| 58 | R-A-P-Q-T-G-G-I-V-D-E-C-C-F-R |
| 59 | A-P-Q-T-G-G-I-V-D-E-C-C-F-R-S |
| 60 | P-Q-T-G-G-I-V-D-E-C-C-F-R-S-C |
| 61 | Q-T-G-G-I-V-D-E-C-C-F-R-S-C-D |
| 62 | T-G-G-I-V-D-E-C-C-F-R-S-C-D-L |
| 63 | G-G-I-V-D-E-C-C-F-R-S-C-D-L-R |
| 64 | G-I-V-D-E-C-C-F-R-S-C-D-L-R-R |

The monoclonal antibody MAb<IGF-1>M-10.7.9 was found to bind to the peptides of SEQ ID NOs: 43 to 49. This corresponds to an epitope as represented by SEQ ID NO:3.

In an analogous manner the epitopes for MAb<IGF-1>11.11.17 and MAb<IGF-1>11.09.15, respectively, have been determined. Both of these monoclonal antibody were found to bind to the peptides of SEQ ID NOs: 43 to 50. This corresponds to an epitope as represented by SEQ ID NO:4.

All references cited in this specification are herewith incorporated by reference with respect to their entire disclosure content and the disclosure content specifically mentioned in this specification.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. An antibody which specifically binds insulin-like growth factor-1 precursor (SEQ ID NO. 1), wherein said antibody comprises a heavy chain variable domain comprising a CDR3H region of SEQ ID NO. 23, a CDR2H region of SEQ ID NO. 24, a CDR1H region of SEQ ID NO. 25, a CDR3L region of SEQ ID NO. 26, a CDR2L region of SEQ ID NO. 27, and a CDR1L region of SEQ ID NO. 28.

* * * * *

SEQUENCE LISTING

<160> NUMBER OF SEQ ID NOS: 64

<210> SEQ ID NO 1
<211> LENGTH: 153
<212> TYPE: PRT
<213> ORGANISM: Homo sapiens

<400> SEQUENCE: 1

```
Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150
```

<210> SEQ ID NO 2
<211> LENGTH: 70
<212> TYPE: PRT
<213> ORGANISM: Homo sapiens

<400> SEQUENCE: 2

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70
```

<210> SEQ ID NO 3
<211> LENGTH: 9
<212> TYPE: PRT
<213> ORGANISM: Homo sapiens

<400> SEQUENCE: 3

```
Pro Thr Gly Tyr Gly Ser Ser Ser Arg
1               5
```

<210> SEQ ID NO 4
<211> LENGTH: 8
<212> TYPE: PRT
<213> ORGANISM: Homo sapiens

```
<400> SEQUENCE: 4

Thr Gly Tyr Gly Ser Ser Ser Arg
1               5

<210> SEQ ID NO 5
<211> LENGTH: 17
<212> TYPE: PRT
<213> ORGANISM: Homo sapiens

<400> SEQUENCE: 5

Asn Lys Pro Thr Gly Tyr Gly Ser Ser Ser Arg Arg Ala Pro Gln Thr
1               5                   10                  15

Gly

<210> SEQ ID NO 6
<211> LENGTH: 4
<212> TYPE: PRT
<213> ORGANISM: Artificial Sequence
<220> FEATURE:
<223> OTHER INFORMATION: linker polypeptide

<400> SEQUENCE: 6

Gly Gly Gly Ser
1

<210> SEQ ID NO 7
<211> LENGTH: 12
<212> TYPE: PRT
<213> ORGANISM: Artificial Sequence
<220> FEATURE:
<223> OTHER INFORMATION: purification tag

<400> SEQUENCE: 7

Gly Ser Arg Lys His His His His His His His His
1               5                   10

<210> SEQ ID NO 8
<211> LENGTH: 134
<212> TYPE: PRT
<213> ORGANISM: Artificial Sequence
<220> FEATURE:
<223> OTHER INFORMATION: FKBP12-IGF-1 fusion polypeptide

<400> SEQUENCE: 8

Met Gly Val Gln Val Glu Thr Ile Ser Pro Gly Asp Gly Arg Thr Phe
1               5                   10                  15

Pro Lys Arg Gly Gln Thr Ala Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Gly Gly Gly Ser Asn Lys Pro Thr Gly Tyr Gly Ser
                85                  90                  95

Ser Ser Arg Arg Ala Pro Gln Thr Gly Gly Gly Ser Thr Leu Val Phe
            100                 105                 110

Asp Val Glu Leu Leu Lys Leu Glu Gly Gly Gly Ser Arg Lys His His
        115                 120                 125
```

His His His His His His
    130

<210> SEQ ID NO 9
<211> LENGTH: 322
<212> TYPE: PRT
<213> ORGANISM: Artificial Sequence
<220> FEATURE:
<223> OTHER INFORMATION: SlyD/FKBP12-IGF-1 fusion polypeptide

<400> SEQUENCE: 9

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Gly Gly Ser Gly Gly Gly Ser Gly Gly Gly
                165                 170                 175

Ser Gly Gly Gly Ser Gly Gly Gly Ser Gly Gly Gly Val Gln Val
            180                 185                 190

Glu Thr Ile Ser Pro Gly Asp Gly Arg Thr Phe Pro Lys Arg Gly Gln
        195                 200                 205

Thr Ala Val Val His Tyr Thr Gly Met Leu Glu Asp Gly Lys Lys Phe
    210                 215                 220

Asp Ser Ser Arg Asp Arg Asn Lys Pro Phe Lys Phe Met Leu Gly Lys
225                 230                 235                 240

Gln Glu Val Ile Arg Gly Trp Glu Glu Gly Val Ala Gln Met Ser Val
                245                 250                 255

Gly Gln Arg Ala Lys Leu Thr Ile Ser Pro Asp Tyr Ala Tyr Gly Gly
            260                 265                 270

Gly Gly Ser Asn Lys Pro Thr Gly Tyr Gly Ser Ser Ser Arg Arg Ala
        275                 280                 285

Pro Gln Thr Gly Gly Gly Ser Thr Leu Val Phe Asp Val Glu Leu
    290                 295                 300

Leu Lys Leu Glu Gly Gly Gly Ser Arg Lys His His His His His His
305                 310                 315                 320

His His

<210> SEQ ID NO 10
<211> LENGTH: 130
<212> TYPE: PRT

<213> ORGANISM: Artificial Sequence
<220> FEATURE:
<223> OTHER INFORMATION: Thermus Thermophilus-SlyD-IGF-1 fusion polypeptide

<400> SEQUENCE: 10

Met Arg Gly Ser Lys Val Gly Gln Asp Lys Val Val Thr Ile Arg Tyr
1               5                   10                  15

Thr Leu Gln Val Glu Gly Glu Val Leu Asp Gln Gly Glu Leu Ser Tyr
                20                  25                  30

Leu His Gly His Arg Asn Leu Ile Pro Gly Leu Glu Glu Ala Leu Glu
            35                  40                  45

Gly Arg Glu Glu Gly Glu Ala Phe Gln Ala His Val Pro Ala Glu Lys
    50                  55                  60

Ala Tyr Gly Pro His Gly Asn Lys Pro Thr Gly Tyr Gly Ser Ser Ser
65                  70                  75                  80

Arg Arg Ala Pro Gln Thr Gly Gly Ala Gly Lys Asp Leu Asp Phe Gln
                85                  90                  95

Val Glu Val Val Lys Val Arg Glu Ala Thr Pro Glu Glu Leu Leu His
                100                 105                 110

Gly His Ala His Gly Gly Ser Arg Lys His His His His His His
            115                 120                 125

His His
    130

<210> SEQ ID NO 11
<211> LENGTH: 166
<212> TYPE: PRT
<213> ORGANISM: Artificial Sequence
<220> FEATURE:
<223> OTHER INFORMATION: Thermus Thermophilus-SlyD wild type polypeptide

<400> SEQUENCE: 11

Met Arg Gly Ser Lys Val Gly Gln Asp Lys Val Val Thr Ile Arg Tyr
1               5                   10                  15

Thr Leu Gln Val Glu Gly Glu Val Leu Asp Gln Gly Glu Leu Ser Tyr
                20                  25                  30

Leu His Gly His Arg Asn Leu Ile Pro Gly Leu Glu Glu Ala Leu Glu
            35                  40                  45

Gly Arg Glu Glu Gly Glu Ala Phe Gln Ala His Val Pro Ala Glu Lys
    50                  55                  60

Ala Tyr Gly Pro His Asp Pro Glu Gly Val Gln Val Val Pro Leu Ser
65                  70                  75                  80

Ala Phe Pro Glu Asp Ala Glu Val Val Pro Gly Ala Gln Phe Tyr Ala
                85                  90                  95

Gln Asp Met Glu Gly Asn Pro Met Pro Leu Thr Val Val Ala Val Glu
                100                 105                 110

Gly Glu Glu Val Thr Val Asp Phe Asn His Pro Leu Ala Gly Lys Asp
            115                 120                 125

Leu Asp Phe Gln Val Glu Val Val Lys Val Arg Glu Ala Thr Pro Glu
    130                 135                 140

Glu Leu Leu His Gly His Ala His Gly Gly Ser Arg Lys His His His
145                 150                 155                 160

His His His His His His
                165

<210> SEQ ID NO 12

<211> LENGTH: 119
<212> TYPE: PRT
<213> ORGANISM: Artificial Sequence
<220> FEATURE:
<223> OTHER INFORMATION: Thermus thermophilus SlyD-?IF fusion
    polypeptide

<400> SEQUENCE: 12

Met Arg Gly Ser Lys Val Gly Gln Asp Lys Val Val Thr Ile Arg Tyr
1               5                   10                  15

Thr Leu Gln Val Glu Gly Glu Val Leu Asp Gln Gly Glu Leu Ser Tyr
            20                  25                  30

Leu His Gly His Arg Asn Leu Ile Pro Gly Leu Glu Glu Ala Leu Glu
        35                  40                  45

Gly Arg Glu Glu Gly Glu Ala Phe Gln Ala His Val Pro Ala Glu Lys
    50                  55                  60

Ala Tyr Gly Pro His Gly Ala Gly Ser Gly Ser Gly Ala Gly Lys
65                  70                  75                  80

Asp Leu Asp Phe Gln Val Glu Val Val Lys Val Arg Glu Ala Thr Pro
                85                  90                  95

Glu Glu Leu Leu His Gly His Ala His Gly Gly Ser Arg Lys His
            100                 105                 110

His His His His His His
        115

<210> SEQ ID NO 13
<211> LENGTH: 168
<212> TYPE: PRT
<213> ORGANISM: Artificial Sequence
<220> FEATURE:
<223> OTHER INFORMATION: native SlyD from Thermococcus gammatolerans
    comprising a C-teminal amino acid sequence tag of SEQ ID NO: 16

<400> SEQUENCE: 13

Met Lys Val Glu Arg Gly Asp Phe Val Leu Phe Asn Tyr Val Gly Arg
1               5                   10                  15

Tyr Glu Asn Gly Glu Val Phe Asp Thr Ser Tyr Glu Ser Val Ala Arg
            20                  25                  30

Glu Gln Gly Ile Phe Val Glu Arg Glu Tyr Ser Pro Ile Gly Val
        35                  40                  45

Thr Val Gly Ala Gly Glu Ile Ile Pro Gly Ile Glu Glu Ala Leu Leu
    50                  55                  60

Gly Met Glu Leu Gly Glu Lys Lys Glu Val Val Val Pro Pro Glu Lys
65                  70                  75                  80

Gly Tyr Gly Met Pro Arg Glu Asp Leu Ile Val Pro Val Pro Ile Glu
                85                  90                  95

Gln Phe Thr Ser Ala Gly Leu Glu Pro Val Gly Met Tyr Val Met
            100                 105                 110

Thr Asp Ala Gly Ile Ala Lys Ile Leu Lys Val Glu Glu Lys Thr Val
        115                 120                 125

Arg Leu Asp Phe Asn His Pro Leu Ala Gly Lys Thr Ala Ile Phe Glu
    130                 135                 140

Ile Glu Val Val Glu Ile Lys Lys Ala Gly Glu Ala Gly Gly Ser
145                 150                 155                 160

Arg Lys His His His His His His
            165

<210> SEQ ID NO 14

```
<211> LENGTH: 130
<212> TYPE: PRT
<213> ORGANISM: Artificial Sequence
<220> FEATURE:
<223> OTHER INFORMATION: Thermococcus gammadurans SlyD-IGF-2(53-65)
      fusion polypeptide

<400> SEQUENCE: 14

Met Lys Val Glu Arg Gly Asp Phe Val Leu Phe Asn Tyr Val Gly Arg
1               5                   10                  15

Tyr Glu Asn Gly Glu Val Phe Asp Thr Ser Tyr Glu Ser Val Ala Arg
            20                  25                  30

Glu Gln Gly Ile Phe Val Glu Glu Arg Glu Tyr Ser Pro Ile Gly Val
        35                  40                  45

Thr Val Gly Ala Gly Glu Ile Ile Pro Gly Ile Glu Glu Ala Leu Leu
    50                  55                  60

Gly Met Glu Leu Gly Glu Lys Lys Glu Val Val Pro Pro Glu Lys
65                  70                  75                  80

Gly Tyr Gly Met Pro Gly Ser Arg Val Ser Arg Ser Arg Gly Gly
                85                  90                  95

Ala Gly Lys Thr Ala Ile Phe Glu Ile Glu Val Val Glu Ile Lys Lys
            100                 105                 110

Ala Gly Glu Ala Gly Gly Gly Ser Arg Lys His His His His His
        115                 120                 125

His His
    130

<210> SEQ ID NO 15
<211> LENGTH: 9
<212> TYPE: PRT
<213> ORGANISM: Mus musculus

<400> SEQUENCE: 15

Ser Gly Asp Tyr Tyr Gly Lys Asp Tyr
1               5

<210> SEQ ID NO 16
<211> LENGTH: 17
<212> TYPE: PRT
<213> ORGANISM: Mus musculus

<400> SEQUENCE: 16

Gln Ile Tyr Pro Gly Asp Gly Asp Thr Asn His Asn Gly Lys Phe Lys
1               5                   10                  15

Gly

<210> SEQ ID NO 17
<211> LENGTH: 5
<212> TYPE: PRT
<213> ORGANISM: Mus musculus

<400> SEQUENCE: 17

Ser Tyr Trp Met Asn
1               5

<210> SEQ ID NO 18
<211> LENGTH: 9
<212> TYPE: PRT
<213> ORGANISM: Mus musculus

<400> SEQUENCE: 18
```

-continued

His His Ser Asn Glu Leu Pro His Thr
1               5

<210> SEQ ID NO 19
<211> LENGTH: 7
<212> TYPE: PRT
<213> ORGANISM: Mus musculus

<400> SEQUENCE: 19

Leu Val Ser Asn Arg Glu Ser
1               5

<210> SEQ ID NO 20
<211> LENGTH: 16
<212> TYPE: PRT
<213> ORGANISM: Mus musculus

<400> SEQUENCE: 20

Lys Ala Thr Lys Ser Leu Leu Asn Thr Asp Gly Tyr Thr Tyr Met His
1               5                   10                  15

<210> SEQ ID NO 21
<211> LENGTH: 118
<212> TYPE: PRT
<213> ORGANISM: Mus musculus

<400> SEQUENCE: 21

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn His Asn Gly Lys Phe
        50                  55                  60

Lys Gly Lys Ala Thr Leu Thr Ala Asp Lys Ser Ser Ser Thr Val Tyr
65                  70                  75                  80

Met Gln Leu Ser Ser Leu Thr Ser Glu Asp Ser Ala Val Tyr Phe Cys
                85                  90                  95

Ala Arg Ser Gly Asp Tyr Tyr Gly Lys Asp Tyr Trp Gly Gln Gly Thr
            100                 105                 110

Thr Leu Thr Val Ser Ser
        115

<210> SEQ ID NO 22
<211> LENGTH: 112
<212> TYPE: PRT
<213> ORGANISM: Mus musculus

<400> SEQUENCE: 22

Asp Ile Val Leu Thr Gln Thr Pro Pro Ser Leu Pro Val Asn Met Gly
1               5                   10                  15

Gln Lys Ala Thr Ile Ser Tyr Lys Ala Thr Lys Ser Leu Leu Asn Thr
                20                  25                  30

Asp Gly Tyr Thr Tyr Met His Trp Asn Gln Gln Lys Pro Gly Gln Pro
            35                  40                  45

Pro Lys Leu Leu Ile Tyr Leu Val Ser Asn Arg Glu Ser Gly Val Pro
        50                  55                  60

Asp Arg Phe Ser Gly Ser Gly Ser Gly Thr Asp Phe Thr Leu Asn Ile
65                  70                  75                  80

```
Asn Thr Val Glu Glu Asp Ala Ala Thr Tyr Tyr Cys His His Ser
                85                  90                  95

Asn Glu Leu Pro His Thr Phe Gly Ala Gly Thr Lys Leu Glu Ile Lys
            100                 105                 110

<210> SEQ ID NO 23
<211> LENGTH: 8
<212> TYPE: PRT
<213> ORGANISM: Mus musculus

<400> SEQUENCE: 23

Ile Gly Tyr Tyr Gly Met Asp Tyr
1               5

<210> SEQ ID NO 24
<211> LENGTH: 17
<212> TYPE: PRT
<213> ORGANISM: Mus musculus

<400> SEQUENCE: 24

Gln Ile Tyr Pro Gly Asp Gly Asp Thr Asn Tyr Tyr Gly Asp Phe Lys
1               5                   10                  15

Gly

<210> SEQ ID NO 25
<211> LENGTH: 5
<212> TYPE: PRT
<213> ORGANISM: Mus musculus

<400> SEQUENCE: 25

Asn Leu Trp Met Asn
1               5

<210> SEQ ID NO 26
<211> LENGTH: 8
<212> TYPE: PRT
<213> ORGANISM: Mus musculus

<400> SEQUENCE: 26

Phe Gln Ser Asn Tyr Leu Pro Thr
1               5

<210> SEQ ID NO 27
<211> LENGTH: 7
<212> TYPE: PRT
<213> ORGANISM: Mus musculus

<400> SEQUENCE: 27

Leu Val Ser Asn Arg Phe Ser
1               5

<210> SEQ ID NO 28
<211> LENGTH: 16
<212> TYPE: PRT
<213> ORGANISM: Mus musculus

<400> SEQUENCE: 28

Lys Ser Thr Lys Ser Leu Leu Ser Ser Asp Gly Leu Thr Tyr Leu Asp
1               5                   10                  15

<210> SEQ ID NO 29
<211> LENGTH: 117
<212> TYPE: PRT
```

<213> ORGANISM: Mus musculus

<400> SEQUENCE: 29

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Asn Leu
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Tyr Gly Asp Phe
    50                  55                  60

Lys Gly Lys Ala Thr Leu Thr Ala Asp Ser Ser Ser Thr Ala Tyr
65                  70                  75                  80

Met Gln Leu Ser Arg Leu Thr Ser Glu Asp Ser Ala Val Tyr Phe Cys
            85                  90                  95

Ala Arg Ile Gly Tyr Tyr Gly Met Asp Tyr Trp Gly Gln Gly Thr Ser
            100                 105                 110

Val Thr Val Ser Ser
        115

<210> SEQ ID NO 30
<211> LENGTH: 111
<212> TYPE: PRT
<213> ORGANISM: Mus musculus

<400> SEQUENCE: 30

Asp Val Val Leu Thr Gln Thr Pro Leu Ser Leu Pro Val Asn Ile Gly
1               5                   10                  15

Asp Glu Ala Ser Ile Ser Cys Lys Ser Thr Lys Ser Leu Leu Ser Ser
            20                  25                  30

Asp Gly Leu Thr Tyr Leu Asp Trp Tyr Leu Gln Lys Pro Gly Gln Ser
        35                  40                  45

Pro Gln Val Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ser
            85                  90                  95

Asn Tyr Leu Pro Thr Phe Gly Ala Gly Thr Lys Leu Glu Leu Lys
            100                 105                 110

<210> SEQ ID NO 31
<211> LENGTH: 117
<212> TYPE: PRT
<213> ORGANISM: Mus musculus

<400> SEQUENCE: 31

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Asn Leu
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Tyr Gly Asp Phe
    50                  55                  60

Lys Gly Lys Ala Thr Leu Thr Ala Asp Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Ile Gly Tyr Tyr Gly Met Asp Tyr Trp Gly Gln Gly Thr Ser
            100                 105                 110

Val Thr Val Ser Ser
        115

<210> SEQ ID NO 32
<211> LENGTH: 111
<212> TYPE: PRT
<213> ORGANISM: Mus musculus

<400> SEQUENCE: 32

Asp Val Val Leu Thr Gln Thr Pro Leu Ser Leu Pro Val Asn Ile Gly
1               5                   10                  15

Asp Glu Ala Ser Ile Ser Cys Lys Ser Thr Lys Ser Leu Leu Ser Ser
            20                  25                  30

Asp Gly Leu Thr Tyr Leu Asp Trp Tyr Leu Gln Lys Pro Gly Gln Ser
        35                  40                  45

Pro Gln Val Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ser
                85                  90                  95

Asn Tyr Leu Pro Thr Phe Gly Ala Gly Thr Lys Leu Glu Leu Lys
            100                 105                 110

<210> SEQ ID NO 33
<211> LENGTH: 15
<212> TYPE: PRT
<213> ORGANISM: Homo sapiens

<400> SEQUENCE: 33

Ala Leu Gln Phe Val Cys Gly Asp Arg Gly Phe Tyr Phe Gly Asn
1               5                   10                  15

<210> SEQ ID NO 34
<211> LENGTH: 15
<212> TYPE: PRT
<213> ORGANISM: Homo sapiens

<400> SEQUENCE: 34

Leu Gln Phe Val Cys Gly Asp Arg Gly Phe Tyr Phe Gly Asn Lys
1               5                   10                  15

<210> SEQ ID NO 35
<211> LENGTH: 15
<212> TYPE: PRT
<213> ORGANISM: Homo sapiens

<400> SEQUENCE: 35

Gln Phe Val Cys Gly Asp Arg Gly Phe Tyr Phe Gly Asn Lys Pro
1               5                   10                  15

<210> SEQ ID NO 36
<211> LENGTH: 15
<212> TYPE: PRT
<213> ORGANISM: Homo sapiens

<400> SEQUENCE: 36

```
Phe Val Cys Gly Asp Arg Gly Phe Tyr Phe Gly Asn Lys Pro Thr
1               5                   10                  15
```

<210> SEQ ID NO 37
<211> LENGTH: 15
<212> TYPE: PRT
<213> ORGANISM: Homo sapiens

<400> SEQUENCE: 37

```
Val Cys Gly Asp Arg Gly Phe Tyr Phe Gly Asn Lys Pro Thr Gly
1               5                   10                  15
```

<210> SEQ ID NO 38
<211> LENGTH: 15
<212> TYPE: PRT
<213> ORGANISM: Homo sapiens

<400> SEQUENCE: 38

```
Cys Gly Asp Arg Gly Phe Tyr Phe Gly Asn Lys Pro Thr Gly Tyr
1               5                   10                  15
```

<210> SEQ ID NO 39
<211> LENGTH: 15
<212> TYPE: PRT
<213> ORGANISM: Homo sapiens

<400> SEQUENCE: 39

```
Gly Asp Arg Gly Phe Tyr Phe Gly Asn Lys Pro Thr Gly Tyr Gly
1               5                   10                  15
```

<210> SEQ ID NO 40
<211> LENGTH: 15
<212> TYPE: PRT
<213> ORGANISM: Homo sapiens

<400> SEQUENCE: 40

```
Asp Arg Gly Phe Tyr Phe Gly Asn Lys Pro Thr Gly Tyr Gly Ser
1               5                   10                  15
```

<210> SEQ ID NO 41
<211> LENGTH: 15
<212> TYPE: PRT
<213> ORGANISM: Homo sapiens

<400> SEQUENCE: 41

```
Arg Gly Phe Tyr Phe Gly Asn Lys Pro Thr Gly Tyr Gly Ser Ser
1               5                   10                  15
```

<210> SEQ ID NO 42
<211> LENGTH: 15
<212> TYPE: PRT
<213> ORGANISM: Homo sapiens

<400> SEQUENCE: 42

```
Gly Phe Tyr Phe Gly Asn Lys Pro Thr Gly Tyr Gly Ser Ser Ser
1               5                   10                  15
```

<210> SEQ ID NO 43
<211> LENGTH: 15
<212> TYPE: PRT
<213> ORGANISM: Homo sapiens

<400> SEQUENCE: 43

```
Phe Tyr Phe Gly Asn Lys Pro Thr Gly Tyr Gly Ser Ser Ser Arg
```

<210> SEQ ID NO 44
<211> LENGTH: 15
<212> TYPE: PRT
<213> ORGANISM: Homo sapiens

<400> SEQUENCE: 44

Tyr Phe Gly Asn Lys Pro Thr Gly Tyr Gly Ser Ser Ser Arg Arg
1               5                   10                  15

<210> SEQ ID NO 45
<211> LENGTH: 15
<212> TYPE: PRT
<213> ORGANISM: Homo sapiens

<400> SEQUENCE: 45

Phe Gly Asn Lys Pro Thr Gly Tyr Gly Ser Ser Ser Arg Arg Ala
1               5                   10                  15

<210> SEQ ID NO 46
<211> LENGTH: 15
<212> TYPE: PRT
<213> ORGANISM: Homo sapiens

<400> SEQUENCE: 46

Gly Asn Lys Pro Thr Gly Tyr Gly Ser Ser Ser Arg Arg Ala Pro
1               5                   10                  15

<210> SEQ ID NO 47
<211> LENGTH: 15
<212> TYPE: PRT
<213> ORGANISM: Homo sapiens

<400> SEQUENCE: 47

Asn Lys Pro Thr Gly Tyr Gly Ser Ser Ser Arg Arg Ala Pro Gln
1               5                   10                  15

<210> SEQ ID NO 48
<211> LENGTH: 15
<212> TYPE: PRT
<213> ORGANISM: Homo sapiens

<400> SEQUENCE: 48

Lys Pro Thr Gly Tyr Gly Ser Ser Ser Arg Arg Ala Pro Gln Thr
1               5                   10                  15

<210> SEQ ID NO 49
<211> LENGTH: 15
<212> TYPE: PRT
<213> ORGANISM: Homo sapiens

<400> SEQUENCE: 49

Pro Thr Gly Tyr Gly Ser Ser Ser Arg Arg Ala Pro Gln Thr Gly
1               5                   10                  15

<210> SEQ ID NO 50
<211> LENGTH: 15
<212> TYPE: PRT
<213> ORGANISM: Homo sapiens

<400> SEQUENCE: 50

Thr Gly Tyr Gly Ser Ser Ser Arg Arg Ala Pro Gln Thr Gly Gly
1               5                   10                  15

```
<210> SEQ ID NO 51
<211> LENGTH: 15
<212> TYPE: PRT
<213> ORGANISM: Homo sapiens

<400> SEQUENCE: 51

Gly Tyr Gly Ser Ser Arg Arg Ala Pro Gln Thr Gly Gly Ile
1               5                   10                  15

<210> SEQ ID NO 52
<211> LENGTH: 15
<212> TYPE: PRT
<213> ORGANISM: Homo sapiens

<400> SEQUENCE: 52

Tyr Gly Ser Ser Arg Arg Ala Pro Gln Thr Gly Gly Ile Val
1               5                   10                  15

<210> SEQ ID NO 53
<211> LENGTH: 15
<212> TYPE: PRT
<213> ORGANISM: Homo sapiens

<400> SEQUENCE: 53

Gly Ser Ser Ser Arg Arg Ala Pro Gln Thr Gly Gly Ile Val Asp
1               5                   10                  15

<210> SEQ ID NO 54
<211> LENGTH: 15
<212> TYPE: PRT
<213> ORGANISM: Homo sapiens

<400> SEQUENCE: 54

Ser Ser Ser Arg Arg Ala Pro Gln Thr Gly Gly Ile Val Asp Glu
1               5                   10                  15

<210> SEQ ID NO 55
<211> LENGTH: 15
<212> TYPE: PRT
<213> ORGANISM: Homo sapiens

<400> SEQUENCE: 55

Ser Ser Arg Arg Ala Pro Gln Thr Gly Gly Ile Val Asp Glu Cys
1               5                   10                  15

<210> SEQ ID NO 56
<211> LENGTH: 15
<212> TYPE: PRT
<213> ORGANISM: Homo sapiens

<400> SEQUENCE: 56

Ser Arg Arg Ala Pro Gln Thr Gly Gly Ile Val Asp Glu Cys Cys
1               5                   10                  15

<210> SEQ ID NO 57
<211> LENGTH: 15
<212> TYPE: PRT
<213> ORGANISM: Homo sapiens

<400> SEQUENCE: 57

Arg Arg Ala Pro Gln Thr Gly Gly Ile Val Asp Glu Cys Cys Phe
1               5                   10                  15

<210> SEQ ID NO 58
```

```
<211> LENGTH: 15
<212> TYPE: PRT
<213> ORGANISM: Homo sapiens

<400> SEQUENCE: 58

Arg Ala Pro Gln Thr Gly Gly Ile Val Asp Glu Cys Cys Phe Arg
1               5                   10                  15

<210> SEQ ID NO 59
<211> LENGTH: 15
<212> TYPE: PRT
<213> ORGANISM: Homo sapiens

<400> SEQUENCE: 59

Ala Pro Gln Thr Gly Gly Ile Val Asp Glu Cys Cys Phe Arg Ser
1               5                   10                  15

<210> SEQ ID NO 60
<211> LENGTH: 15
<212> TYPE: PRT
<213> ORGANISM: Homo sapiens

<400> SEQUENCE: 60

Pro Gln Thr Gly Gly Ile Val Asp Glu Cys Cys Phe Arg Ser Cys
1               5                   10                  15

<210> SEQ ID NO 61
<211> LENGTH: 15
<212> TYPE: PRT
<213> ORGANISM: Homo sapiens

<400> SEQUENCE: 61

Gln Thr Gly Gly Ile Val Asp Glu Cys Cys Phe Arg Ser Cys Asp
1               5                   10                  15

<210> SEQ ID NO 62
<211> LENGTH: 15
<212> TYPE: PRT
<213> ORGANISM: Homo sapiens

<400> SEQUENCE: 62

Thr Gly Gly Ile Val Asp Glu Cys Cys Phe Arg Ser Cys Asp Leu
1               5                   10                  15

<210> SEQ ID NO 63
<211> LENGTH: 15
<212> TYPE: PRT
<213> ORGANISM: Homo sapiens

<400> SEQUENCE: 63

Gly Gly Ile Val Asp Glu Cys Cys Phe Arg Ser Cys Asp Leu Arg
1               5                   10                  15

<210> SEQ ID NO 64
<211> LENGTH: 15
<212> TYPE: PRT
<213> ORGANISM: Homo sapiens

<400> SEQUENCE: 64

Gly Ile Val Asp Glu Cys Cys Phe Arg Ser Cys Asp Leu Arg Arg
1               5                   10                  15
```